US012414986B2

(12) United States Patent
Nicolson

(10) Patent No.: US 12,414,986 B2
(45) Date of Patent: Sep. 16, 2025

(54) USE OF GLUTAMINE SYNTHETASE FOR TREATING FATTY LIVER DISEASE

(71) Applicant: THOERIS GMBH, Vienna (AT)

(72) Inventor: Tamara Nicolson, Vienna (AT)

(73) Assignee: Thoeris GmbH, Vienna (AT)

( * ) Notice: Subject to any disclaimer, the term of this patent is extended or adjusted under 35 U.S.C. 154(b) by 1054 days.

(21) Appl. No.: 17/281,240

(22) PCT Filed: Sep. 28, 2019

(86) PCT No.: PCT/EP2019/076334

§ 371 (c)(1),
(2) Date: Mar. 29, 2021

(87) PCT Pub. No.: WO2020/065082

PCT Pub. Date: Apr. 2, 2020

(65) Prior Publication Data

US 2022/0218802 A1 Jul. 14, 2022

(30) Foreign Application Priority Data

Sep. 28, 2018 (GB) ..................................... 1815892

(51) Int. Cl.

| | |
|---|---|
| ***A61K 38/53*** | (2006.01) |
| ***A61K 31/19*** | (2006.01) |
| ***A61K 47/60*** | (2017.01) |
| ***A61P 1/16*** | (2006.01) |
| ***C12N 9/00*** | (2006.01) |

(52) U.S. Cl.

CPC .............. *A61K 38/53* (2013.01); *A61K 31/19* (2013.01); *A61K 47/60* (2017.08); *A61P 1/16* (2018.01); *C12N 9/93* (2013.01); *C12Y 603/01002* (2013.01); *C07K 2319/21* (2013.01)

(58) Field of Classification Search

CPC ........ A61K 38/53; A61K 31/19; A61K 47/60; A61K 31/216; A61K 31/235; A61K 31/437; A61P 1/16; C12N 9/93; C12Y 603/01002; C07K 2319/21

See application file for complete search history.

(56) References Cited

FOREIGN PATENT DOCUMENTS

| | | | | |
|---|---|---|---|---|
| MX | 2014013566 A | | 5/2016 | |
| WO | WO-2016085887 A1 | * | 6/2016 | ........... A61K 31/192 |
| WO | 2018215780 A1 | | 11/2018 | |

OTHER PUBLICATIONS

Zhou et al., Neurochemistry International, 2020, vol. 140, 104809, p. 1-18. (Year: 2020).*

Qvartskhava et al., Proc Natl Acad Sci U S A. Apr. 28, 2015;112(17):5521-6. doi: 10.1073/pnas.1423968112. Epub Apr. 13, 2015. PMID: 25870278; PMCID: PMC4418919. (Year: 2015).*

United Kingdom Intellectual Property Office, Search Report for GB Application No. GB1815892.3, dated Jun. 7, 2019, United Kingdom.

International Searching Authority, Written Opinion of the International Searching Authority, PCT Application No. PCT/EP2019/076334, dated Oct. 17, 2019.

International Searching Authority, International Search Report, PCT Application No. PCT/EP2019/076334, dated Oct. 17, 2019.

Torres-Vega et al., "Delivery of glutamine synthetase gene by baculovirus vectors: a proof of concept for the treatment of acute hyperammonemia," Gene Therapy, Oct. 23, 2014, 22(1): 58-64, Macmillan Publishers Limited, GB.

Wang Ning et al., "The bioreactor with CYP3A4- and glutamine synthetase-introduced HepG2 cells: treatment of hepatic failure dog with diazepam overdosage," Artificial Organs, Aug. 2005, 29(8): 681-684, ISSN: 0160-564X.

Wright et al., "Interorgan ammonia metabolism in liver failure: the basis of current and future therapies," Liver International, Feb. 2011, 31(2): 163-175, ISSN: 1478-3231.

Haberle et al., "Clinical and biochemical aspects of primary and secondary hyperammonemic disorders," Archives of Biochemistry and Biophysics, Apr. 27, 2013, 536(2): 101-108, SSN: 0003-9861, Academic Press, US.

Database Geneseq [Online], "PRO polypeptide Seq ID No. 46," retrieved from EBI accession No. GSP: ADY14240, Database accession No. ADY14240, Jun. 15, 2007.

* cited by examiner

*Primary Examiner* — Kade Ariani

(74) *Attorney, Agent, or Firm* — Reichel Stohry Dean LLP; Natalie J. Dean

(57) ABSTRACT

The present invention relates to the treatment of fatty liver disease, by administration of glutamine synthetase.

17 Claims, 10 Drawing Sheets

Specification includes a Sequence Listing.

Control vs AM535 dosed (40 x light microscope)

USE OF GLUTAMINE SYNTHETASE FOR TREATING FATTY LIVER DISEASE

PRIORITY

The present application is related to, claims the priority benefit of, and is a 35 U.S.C. 371 national stage application of International Patent Application No. PCT/EP2019/076334, filed Sep. 28, 2019, which is related to and claims the priority benefit of Great Britain Patent Application No. 1815892.3, filed Sep. 28, 2018. The entire contents of each of the aforementioned priority applications are hereby expressly incorporated herein by reference in their entireties.

TECHNICAL FIELD

The present invention relates to the use of glutamine synthetase for the treatment of fatty liver disease. Also provided is a pharmaceutical composition comprising glutamine synthetase.

BACKGROUND

A healthy liver typically would not contain any, or very little, fat. Both alcoholic and non-alcoholic liver diseases at an early stage are marked by the appearance of fat deposits in the liver. Alcohol Related Liver Disease (ARLD), caused by excess alcohol intake, increases in severity if left untreated from the appearance of fat deposits, to hepatitis, and cirrhosis. At its most severe, ARLD may progress to liver cancer. Similarly, non-alcoholic related fatty liver disease (NAFLD) begins with the build up of fat in the liver, typically in people who are overweight or obese. NAFLD also has several stages of severity, from fatty liver deposits in the liver to fibrosis, scarring and cirrhosis of the liver. Currently, there is no treatment for fatty liver disease, apart from changes to alcohol intake and modifications to diet and lifestyle.

Fatty liver disease may be referred to as steatosis or simple steatosis. Accumulation of fat may be accompanied by inflammation, which is a condition known as steatohepatitis and is more progressive than simple fatty liver or simple steatosis.

NAFLD may be caused by metabolic factors, some of which may have a genetic cause such as glycogen storage diseases, Weber-Christian disease etc. Other causes include poor nutrition, malnutrition, and the use of drugs or toxins including chemotherapies and antiretroviral therapies.

The pathology of fatty liver disease is represented by the appearance of small fat vacuoles around the nucleus of a liver cell. As the size of the vacuoles increases, the nucleus may be pushed to the periphery of the cell, giving the cell a signet ring appearance. As the fats dissolve during tissue processing, the vacuoles often appear empty. Large vacuoles which coalesce may form cysts, which are considered to be irreversible.

Management of the condition may also include dietary control to restrict protein intake and ensure adequate nutritional intake, including management of protein and/or nitrogen intake and parenteral intake of calories.

However, despite improvements in treatment and management of the condition current therapies are non-specific and do not always succeed in managing the condition successfully. There is therefore a continuing need for further or improved therapies for fatty liver disease.

BRIEF SUMMARY

The present invention seeks to address this need and is based on the concept of using glutamine synthetase to treat fatty liver disease.

In particular, the present invention provides glutamine synthetase for use in treating fatty liver disease by reducing the amount of fat deposits in the liver of a subject. Glutamine synthetase may be provided to a subject as a nucleic acid molecule, as gene therapy. Alternatively, it may be administered as a protein therapy.

Glutamine synthetase (GS) catalyses the reaction:

$$\text{Glutamate+ATP+NH}_3\rightarrow\text{Glutamine+ADP+phosphate.}$$

The present invention is based on the surprising observation that administration of glutamine synthetase reverses the symptoms of fatty liver in liver cells. Specifically, glutamine synthetase has been shown to have the effect of reducing or eliminating fat deposits in liver cells.

The present invention is also based on the surprising observation that administration of glutamine synthetase prevents the progression of fibrosis in liver tissue. Specifically, glutamine synthetase has been shown to have the effect of reducing or eliminating fibrosis in liver tissue.

Glutamine is an important amino acid that has a multitude of functions including maintenance of the gut permeability and of immune function, both of which may contribute to this unexpected action observed action of glutamine synthase in the treatment of NAFLD.

Additionally, the combined use of GS and an ammonia lowering agent (such as a nitrogen scavenger, for example, a pharmaceutically acceptable salt of phenylacetic acid, such as sodium phenylacetate) has a synergistic effect and may further increase the ability of GS to reduce or eliminate fat deposits in the liver.

Accordingly, in one aspect the present invention provides glutamine synthetase (GS) for use in treating fatty liver disease by reducing or eliminating fat deposits in the liver. GS reduces or ameliorates cellular effects of fatty liver disease, such as fat deposits in liver cells or tissue, and therefore reverses or prevents the progression of fatty liver disease in liver tissue, in particular simple fatty liver disease. Therefore, the present invention provides GS for use in a method of treating or preventing fatty liver disease and associated liver disease including hepatitis, fibrosis, cirrhosis and cancer.

In a suitable embodiment, GS is provided for use in treating fatty liver diseases by reducing or eliminating fat deposits in the liver, may be for use in combination with an ammonia lowering agent.

In another aspect, the invention provides an ammonia lowering agent for use in combination with GS, for use in treating fatty liver disease by reducing or eliminating fat deposits in the liver.

A related aspect of the invention also provides use of GS for the manufacture of a composition (e.g. a pharmaceutical or nutritional composition, for example a medicament or supplement) for the treatment of fatty liver disease by reducing or eliminating fat deposits in the liver.

In a suitable embodiment, the composition may be for use in combination with an ammonia lowering agent.

A further aspect of the invention also provides use of an ammonia lowering agent for the manufacture of a composition for use in combination with GS for the treatment of fatty liver disease by reducing or eliminating fat deposits in the liver.

In a further aspect the present invention provides use of GS and an ammonia lowering agent for the manufacture of a composition for use in the treatment of fatty liver disease by reducing or eliminating fat deposits in the liver.

In a further aspect the present invention provides a method of treating fatty liver disease in a subject by reducing or eliminating fat deposits in the liver, comprising administering GS to a said subject (more particularly to a subject in need thereof). In a suitable embodiment, the method further comprises administering an ammonia lowering agent. In a suitable embodiment, the method may comprise simultaneous, sequential or subsequent administration of glutamine synthetase (GS) and an ammonia lowering agent to said subject. A method of the invention may comprise a step of diagnosing a subject with fatty liver disease. A method of the invention may comprise monitoring a subject with fatty liver disease during and after treatment.

Also provided is a composition comprising GS, for use in treating fatty liver disease by reducing or eliminating fat deposits in the liver to a subject.

Suitably, the composition comprising GS may be a pharmaceutical or nutritional composition, for example a medicament or supplement. Suitably, the composition may further comprise an ammonia lowering agent.

The invention also relates to a composition comprising GS and an ammonia lowering agent.

Suitably the composition may be a pharmaceutical or nutritional composition. Suitably, the composition may be for use in treating fatty liver disease by reducing or eliminating fat deposits in the liver.

In another aspect, the invention provides a cell comprising an expression vector selected from the group consisting of: an expression vector encoding glutamine synthetase or a biologically active fragment or variant thereof, for use in the treatment of fatty liver disease, and an expression vector encoding glutamine synthetase or a biologically active fragment or variant thereof, for use in combination with an ammonia lowering agent, for use in the treatment of fatty liver disease.

In another aspect, the invention provides a kit comprising an expression vector encoding glutamine synthetase or a biologically active fragment or variant thereof, and a further therapeutic agent. Suitably, the further therapeutic agent may be an agent that is effective against fatty liver disease. Suitably the agent that is effective against fatty liver disease is an ammonia lowering agent or an amino acid or urea cycle intermediate thereof. The kit may be provided for use in a method of treating fatty liver disease.

In another aspect, the invention provides a product comprising GS and a further therapeutic agent, as a combined preparation for separate, simultaneous or sequential use in treating fatty liver disease. Suitably, the further therapeutic agent may be an agent that is effective against fatty liver disease. Suitably the agent that is effective against hyperammonemia is an ammonia lowering agent or an amino acid or urea cycle intermediate thereof. More suitably, the further therapeutic agent is a nitrogen scavenger.

In another aspect the present invention provides glutamine synthetase (GS) for use in treating late stage fatty liver disease by reducing or eliminating fibrosis in the liver. Therefore, GS reverses or prevents the progression of fatty liver disease, in particular advanced or late stage fatty liver disease and cirrhosis. Therefore, the present invention provides GS for use in a method of treating or preventing late stage fatty liver disease including hepatitis, fibrosis, cirrhosis and cancer by reducing or eliminating fibrosis in the liver.

In a suitable embodiment, the composition may be for use in combination with an ammonia lowering agent.

In another aspect, the invention provides an ammonia lowering agent for use in combination with GS, for use in treating fatty liver disease by reducing or eliminating fibrosis in the liver.

A related aspect of the invention also provides use of GS for the manufacture of a composition (e.g. a pharmaceutical or nutritional composition, for example a medicament or supplement) for the treatment of fatty liver disease by reducing or eliminating fibrosis in the liver.

In a suitable embodiment, there may be provided use of GS for the manufacture of a composition (e.g. a pharmaceutical or nutritional composition, for example a medicament or supplement) for use in combination with an ammonia lowering agent for the treatment of fatty liver disease by reducing or eliminating fibrosis in the liver. The composition may be for combined, simultaneous, separate or sequential administration of GS and the ammonia lowering agent.

A further aspect of the invention also provides use of an ammonia lowering agent for the manufacture of a composition for use in combination with GS for the treatment of fatty liver disease by reducing or eliminating fibrosis in the liver.

In a further aspect the present invention provides use of GS and an ammonia lowering agent for the manufacture of a composition for use in the treatment of fatty liver disease by reducing or eliminating fibrosis in the liver.

In a further aspect the present invention provides a method of treating fatty liver disease in a subject by reducing or eliminating fibrosis in the liver, comprising administering GS to a said subject (more particularly to a subject in need thereof). In a suitable embodiment, the method further comprises administering an ammonia lowering agent. In a suitable embodiment, the method may comprise simultaneous, sequential or subsequent administration of glutamine synthetase (GS) and an ammonia lowering agent to said subject. A method of the invention may comprise a step of diagnosing a subject with fatty liver disease. A method of the invention may comprise monitoring a subject with fatty liver disease during and after treatment.

Also provided is a composition comprising GS, for use in treating fatty liver disease by reducing or eliminating fibrosis in the liver to a subject.

Suitably, the composition comprising GS may be a pharmaceutical or nutritional composition, for example a medicament or supplement. Suitably, the composition may further comprise an ammonia lowering agent.

The invention also relates to a composition comprising GS and an ammonia lowering agent.

Suitably the composition may be a pharmaceutical or nutritional composition. Suitably, the composition may be for use in treating fatty liver disease by reducing or eliminating fibrosis in the liver.

In another aspect, the invention provides a cell comprising an expression vector selected from the group consisting of: an expression vector encoding glutamine synthetase or a biologically active fragment or variant thereof, for use in the treatment of fatty liver disease, and an expression vector encoding glutamine synthetase or a biologically active fragment or variant thereof, for use in combination with an ammonia lowering agent, for use in the treatment of fatty liver disease by reducing or eliminating fibrosis in the liver.

In another aspect, a kit as defined herein may be provided for use in a method of treating fatty liver disease by reducing or eliminating fibrosis in the liver.

In another aspect, the invention provides a product comprising GS and a further therapeutic agent, as a combined preparation for separate, simultaneous or sequential use in treating fatty liver disease reducing or eliminating fibrosis in the liver. Suitably, the further therapeutic agent may be an agent that is effective against fatty liver disease. Suitably the agent that is effective against hyperammonemia is an ammonia lowering agent or an amino acid or urea cycle intermediate thereof. More suitably, the further therapeutic agent is a nitrogen scavenger.

DETAILED DESCRIPTION

The present invention may be used for the treatment of a subject having acquired or genetic fatty liver disease. The subject may have genetic (inherited) fatty liver disease associated with a urea cycle disorder (UCD). The subject may have a genetic disorder due to deficiency of a urea cycle enzyme or transporter. Therefore, the present invention relates to the treatment of a subject having fatty liver disease, wherein the subject has a UCD, or other genetically acquired hyperammonemic disease, preferably a deficiency of ornithine transcarbamylase (i.e a mutation or genetic abnormality in the ornithine transcarbamylase gene which leads to abnormal expression of the protein). A subject having a UCD or other genetically acquired hyperammonemia may show symptoms of fatty liver disease, for example fat deposits in liver cells or fibrosis of liver tissue. The subject may have a genetic disorder such as a glycogen storage disorder or Christian Weber disease, which is associated with fatty liver disease. The subject may have acquired fatty liver disease, and may have one or more conditions selected from the group consisting of diabetes, obesity, malnutrition, excess alcohol intake, and drug use. The subject may have one of the afore-mentioned conditions and is diagnosed as being at risk of developing fatty liver disease.

The invention as described herein also relates to treating liver tissue removed from a subject, for example in an ex vivo method of treatment.

The term “GS” may include either a GS protein, or a nucleic acid sequence encoding a GS protein or an active fragment thereof. GS herein includes within its scope any biologically active fragment or variant of the protein or nucleic acid sequence. The term “GS protein” may alternatively be expressed as “a protein having glutamine synthetase (GS) activity”. The term “protein” is used broadly used herein to include any proteinaceous molecule, including peptides and polypeptides, as well as protein or polypeptide fragments; the GS protein does not have to be, or to correspond to, a full length GS enzyme as it appears in nature (e.g. a native or wild-type GS) and truncated or other variants are included, as described more detail below. Also included are conjugates, or fusions, of the GS protein with other molecules, as also described in more detail below.

The term “fatty liver disease” includes any condition in which fat deposits are present in liver cells. Such conditions include genetic or acquired fatty liver disease (steatosis) including ARLD and NAFLD and conditions derived from fatty liver disease such as inflammation of the liver (steatohepatitis including NASH), hepatitis (alcoholic and non-alcoholic), cirrhosis, fibrosis, and liver cancer. The aspects of the present invention may be used for reducing or eliminating fat deposits in the liver, and/or reversing fibrosis or scarring of the liver either wholly or partially. The aspects of the present invention may also be used for inhibiting or reversing progression of fatty liver disease, for example slowing or preventing the progress of disease from simple fatty liver to steatohepatitis (including NASH), fibrosis, from fibrosis, cirrhosis, or liver cancer. The aspects of the present invention relate to treatment or prevention of disease by reversal of the symptoms of disease, for example reversal of the symptoms of fatty liver and/or fibrosis. Therefore, the aspects of the invention relate to reducing or eliminating fat deposits and/or scarring in the liver. Therefore, the aspects of the present invention relate to treating or preventing fatty liver disease and associated liver disease including hepatitis, fibrosis, cirrhosis and cancer.

In fatty liver disease, elevated ammonia levels may be observed. Thus, a plasma (or blood) ammonia concentration of >40, 60 or 70 or 80 μmol/L or more, e.g. 41, 42, 45, 50, 55, 60, 70 or 80 μmol/L or more may be observed. For example, a plasma ammonia concentration of >100 μmol/L, and particularly 150 μmol/L or higher, where associated with a normal anion gap and a normal plasma glucose concentration, may or may not be related to fatty liver disease, for example due to changes in the expression and/or activity of a urea cycle enzyme (UCE).

Fatty liver disease may be detected using imaging procedures for example ultrasound, CT scanning, or MRI; blood tests (e.g. in plasma or serum or any blood-derived sample) for higher than normal levels of liver enzymes such as alanine amino transferase and aspartate amino transferase according to techniques well known and used in the art; measurement of the collagen proportionate area in liver tissue by staining, or a liver biopsy to detect symptoms such as fat deposits or fibrosis or scarring in the liver or liver tissue. Such determinations and analyses may be combined with clinical assessments, e.g. liver function tests etc. Investigations of family history and/or molecular genetic tests and/or assessments may also be undertaken. Therefore, the present invention may include a step of diagnosing a subject for fatty liver disease, for symptoms of hyperammonemia, or for genetic disorders resulting in fatty liver (for example a UCD) or hyperammonemia. In other aspects of the invention, the subject is one who has been diagnosed as having fatty liver disease, or as having a genetic disorder resulting in fatty liver (for example a UCD) or a condition which results in a higher risk of fatty liver disease, for example diabetes, obesity, malnutrition, excess alcohol intake, or drug use.

Herein, the internal designation AM-535 refers to glutamine synthetase, and may include human GS with one or more N terminal linkers and optionally a poly(his) tag. It may include pegylated versions of GS. AM-535 is further described in the Examples. As used herein, reference to a glutamine synthetase or GS protein for use according to the present invention includes reference to all forms of enzymatically-active GS, including human GS and GS from non-human animals (such as mouse, cow, rabbit, rat, monkey, chimpanzee, and dog etc), or from other sources including for example fungi, plants or bacteria, as well as enzymatically-active variants. Representative GS proteins thus include those having at least 50%, 55%, 60%, 65%, 70%, 75%, 80%, 85%, 90%, 91%, 92%, 93%, 94%, 95%, 96%, 97%, 98%, 99% or more sequence identity with the GS polypeptide set forth in SEQ ID NO:1 or 2 or 4 (human GS, precursor, mature and N-terminal tagged forms respectively) or with the GS polypeptide set forth in SEQ ID NO. 6 (GS from *Lactobacillus acidophilus* strain 30SC) or SEQ ID NO. 7 (GS from corn, *Zea mays*), or an enzymatically-active fragment thereof. For example, reference to GS may also include N- and/or C-terminally truncated polypeptides or amino acid modified protein (e.g. post-translational modifications, such as adenylation, or other modifications such as amino acid polymorphisms that may affect the structure or activity of the protein). It may also include multimers of the protein. The term "GS protein" thus includes all native forms of GS enzymes or polypeptides as well as enzymatically-active fragments or variants thereof, including synthetically derived and modified polypeptides having one or more amino acid substitutions, additions (including insertions and extensions) or deletions, which retain GS enzymatic activity.

The GS may thus be, or may be derived from, any enzyme falling within the enzyme classification EC 6.3.1.2. It may be any polypeptide or peptide having GS activity. GS activity may be defined as the ability to convert glutamate and ammonia to glutamine, e.g. according to the reaction scheme set out above. GS activity may be assessed or determined using assays or tests (e.g. a functional activity assay) as known in the art and described in the literature. For example, GS enzyme activity assays are described in Listrom et al, Biochem. J. 1997, 328, 159-163. An assay for GS activity is also described in the Examples below (see Examples 2 and 4).

Human GS is expressed as a polypeptide of 373 amino acids (as shown in SEQ ID NO. 1). This represents the full "precursor" protein as expressed which is then further processed to a mature form having amino acids 2-373 (only the N-terminal methionine is removed to yield a mature protein of 372 amino acids in vivo, as shown in SEQ ID NO. 2. The exemplary polynucleotide set forth in SEQ ID NO. 3 represents a cDNA encoding the polypeptide of SEQ ID NO. 1. SEQ ID NO. 4 represents a modified human GS protein, comprising the GS polypeptide of SEQ ID NO. 1 provided with an N-terminal His-tag and linker sequence, as prepared and used in the Examples below. SEQ ID NO. 5 is a cDNA sequence encoding the polypeptide of SEQ ID NO. 4, codon-optimised for expression in bacteria, as used in the Examples below.

Human GS has been well-characterised (see for example Listrom et al., 1997, supra). GS enzymes from other organisms, including plants and bacteria, have also been identified, and nucleic acid and amino acid sequences of such other GS enzymes are well known in the art and provided in freely-available databases, such as, for example, the National Center for Biotechnology Information (NCBI) Nucleotide (ncbi.nlm.nih.gov/nuccore) and Protein (ncbi.nlm.nih.gov/protein) databases. Although the sequence identity between plant or bacterial GS enzymes and human GS may be low, the structural and functional similarity is high. Accordingly, plant or bacterial GS, or indeed GS from other organisms, or amino acid sequence variants thereof, may be used. By way of representative example, SEQ ID NO. 6 sets forth the amino acid sequence of the GS from *Lactobacillus acidophilus* strain 30SC, which has 23.8% sequence identity with human GS and 61.9% sequence identity with the GS of *Lactobacillus casei*, and SEQ ID NO. 7 sets forth the amino acid sequence of the GS from corn (maize, *Zea mays*), which has 55.7% sequence identity with human GS.

GS commonly occurs as a multimer comprising multiple (i.e. 2 or more) monomer subunits. The GS amino acid sequence provided above, for example, represents such a monomer subunit. Human GS is most frequently reported as a pentamer or decamer (5 or 10 subunits). As used herein, the GS may be provided as a monomer and/or as a multimer. The multimer may comprise 2 or more monomer subunits, for example 2 to 20, 2 to 16, 2 to 15, 2 to 14 or 2 to 12 subunits. Recombinant GS may be present as a pentamer, a decamer, or other multimers, or as an active monomer.

The GS protein used in the methods provided herein can be obtained by any method known in art, such as recombinant methods, protein isolation and purification methods and chemical synthesis methods, providing the resulting GS exhibits enzymatic activity. Accordingly, the GS can be recombinant GS, native GS isolated from tissue, or chemically synthesized GS.

It is well within the capabilities of a skilled person to modify a GS polypeptide, such as the polypeptide set forth in SEQ ID NO:1, to generate enzymatically-active GS variants for use in the methods provided herein. For example, a person skilled in the art would understand that modifications at positions involved in substrate binding, or in the active site, are less likely to be tolerated than modifications at positions outside these critical regions. Any GS polypeptide can be tested using methods well known in the art, such as those described in the art.

The GS polypeptide may be operably linked to one or more linker and/or tag sequences. A linker sequence may be suitable any peptide sequence, suitably of 1 to 30 amino acids, more suitably of 1 to 20 amino acids, more suitably 1 to 10 amino acids. Most suitable linker sequences may be 3, 4, 5, 6, 7, 8, 9 or 10 amino acids in length. Suitably, a linker sequence may comprise glycine and/or serine residues to provide flexibility. A most suitable linker may be GGGS or GGGGS. GS may be operably linked to two or more linkers, which may be the same or may be different. Suitably, one or more linkers may be operably linked (directly, or indirectly via another peptide sequence) to the N terminus of the polypeptide. Where two or more linkers are provided, any one linker sequence may be directly operably linked to another linker, or indirectly linked to another vector via an intervening sequence. A tag sequence may be any peptide sequence, suitably which binds to a matrix for isolation of the protein. Suitable tags are known and available in the art, and include for example chitin binding protein (CBE), maltose binding protein (MBP), Strep-tag and glutathione-S-transferase (GST), and poly(His) tag. A poly(his) tag may be HHHHHH, or any suitable number of His residues. In a suitable embodiment, the GS sequence used in the present invention may be provided in the following conformation: linker-tag-linker-GS. Most suitably, the linkers may be as defined above, and more suitably GGGS or GGGGS. The tag may be as defined above, and most suitably a poly(his) tag. Most suitably, the GS sequence may be provided as GGGS-poly (his)-GGGGS-GS. Suitably, the GS sequence is provided as GGGS-poly(his)-GGGGS-human GS. Suitably, human GS is SEQ ID NO 1. A nucleic acid sequence encoding the GS protein and any linker and/or tag sequences as defined herein is also provided. Such a nucleic acid sequence may be provided in a vector, as described herein.

Where GS is provided as a nucleic acid molecule, it may be the full length native sequence encoding GS, for example a sequence as shown in SEQ ID NO. 2, or may be a biologically active fragment or variant thereof. The term "biologically active" refers to a fragment or variant of the nucleic acid encoding glutamine synthetase (SEQ. ID NO: 1) exhibiting the ability to convert glutamate to glutamine. The protein according to SEQ ID NO: 1 is encoded by the nucleic acid sequence according to SEQ ID NO: 2. The nucleic acid molecule encoding GS or a biologically active fragment or variant thereof may be provided in a vector. The vector may be an expression vector.

The vector, may comprise a fragment or variant of SEQ ID NO:2 which encodes a biologically active fragment or variant of glutamine synthetase.

In a suitable embodiment, the vector further encodes an ammonia lowering agent.

The term "variant" as used herein refers to a polypeptide comprising an alteration of the primary structure of the polypeptide of SEQ ID NO: 1. Suitably, a variant may share 70% or more identity with the polypeptide of SEQ ID NO: 1; 80% or more identity with the polypeptide of SEQ ID NO: 1; 90% or more identity with the polypeptide of SEQ ID NO: 1; 95% or more identity with the polypeptide of SEQ ID NO: 1; 96% or more identity with the polypeptide of SEQ ID NO: 1; 97% or more identity with the polypeptide of SEQ ID NO: 1; 98% or more identity with the polypeptide of SEQ ID NO: 1; or even 99% or more identity with polypeptide of SEQ ID NO: 1. A variant may differ from the polypeptide of SEQ ID NO: 1 by 1% or more, 2% or more, 3% or more, 4% or more, 5% or more, 10% or more, 20% or more, or even 30% or more with reference to sequence according to SEQ ID NO: 1.

The term "fragment" as used herein refers to a polypeptide comprising an alteration to the length of the primary structure of the polypeptide of SEQ ID NO: 1. A suitable fragment may comprise at least 60%, at least 65%, at least 70%, at least 75%, at least 80%, at least 85%, at least 90%, or at least 95% of the full length of SEQ ID NO: 1. Indeed, a suitable variant may comprise at least 96%, at least 97%, at least 98%, or at least 99% of SEQ ID NO: 1.

In a suitable embodiment, the expression vector may be viral or non-viral. By way of example, a suitable viral expression vector may be derived from a virus selected from the group consisting of paramyxovirus, retrovirus, adenovirus, lentivirus, pox virus, alphavirus, and herpes virus. Other suitable viral vectors will be known to those skilled in the art.

Suitable non-viral expression vectors may be selected from the group consisting of inorganic particle expression vectors (such as calcium phosphate, silica, and gold), lipid based particle expression vectors (for example cationic lipids, lipid nano emulsions, and solid lipid nanoparticles) and polymer based particle expression vectors (for example peptides, polyethylenimine, chitosan, and dendimers). Other suitable non-viral expression vectors will be known to those skilled in the art.

The term also includes a pro-drug for the GS protein, that is a form which does not in itself exhibit GS activity, but which may be converted to an active GS upon administration to the subject.

Thus, as used herein, "enzymatically-active" with reference to a GS protein or polypeptide refers to a GS protein or polypeptide that can catalyze the conversion of glutamate and ammonia to glutamine. Typically, the enzymatically-active GS protein or polypeptide exhibits at least or about 30%, 40%, 50%, 60%, 70%, 80%, 90%, 95%, 96%, 97%, 98% or 99% of the enzymatic activity of a GS polypeptide as set forth in SEQ ID NO:1, 2, 4, 6 or 7.

The term "subject" as used herein includes any human or non-human animal and particularly refers to mammals, including for example humans, primates, livestock animals (e.g. sheep, pigs, cattle, horses, donkeys), laboratory test animals (eg. mice, rabbits, rats, guinea pigs), companion animals (e.g. dogs, cats) and captive wild animals (eg. foxes, kangaroos, deer). Preferably, the mammal is human or a laboratory test animal. Even more preferably, the mammal is a human.

As used herein the terms "treating", "treatment", "preventing" and "prevention" refer to any and all uses which remedy or ameliorate a condition or symptoms, prevent the establishment of a condition or disease, or otherwise prevent, hinder, retard, reduce or reverse the progression of a condition or disease or other undesirable symptoms in any way whatsoever. Specifically, in the present invention "treating" means reversing the symptoms of fatty liver disease by reducing or eliminating fat deposits in the liver, wholly or partially. In this manner, vacuoles of triglycerides present in the liver shrink or are eliminated. Progressive symptoms of liver disease such as inflammation, fibrosis or scarring, may also be reversed wholly or partially. Thus the terms "treating" and "preventing" and the like are to be considered in their broadest context. For example, treatment does not necessarily imply that a patient is treated until total recovery, but includes any improvement or amelioration in the condition of a patient or subject, or in a symptom of the disease or condition. Thus for example in the case of genetic, rather than acquired fatty liver disease, treatment according to the present invention does not of course treat the underlying genetic disorder, but rather the resulting clinical condition of fatty liver disease. In conditions which display or are characterized by multiple symptoms, the treatment or prevention need not necessarily remedy, ameliorate, prevent, hinder, retard, reduce or reverse all of said symptoms, but may remedy, ameliorate, prevent, hinder, retard, reduce or reverse one or more of said symptoms. In a suitable embodiment, "treatment" according to the present invention leads to a reduction in the levels of fat in the liver for example to normal or healthy levels, e.g. no fat or very minimal fat vacuoles present; absence of fat cysts; cell nucleus's being normal and no displacement, no fibrosis or minimal/healthy levels of fibrosis. Thus, treatment includes the restoration of normal or healthy liver fat levels. Treatment may also include the reduction or elimination of fibrosis in liver tissue.

In a suitable embodiment, "treatment" according to the present invention may include an increase in glutamine synthetase levels and/or activity in subject's tissue. Such an increase may be in any suitable tissue (for example liver). An increase in glutamine synthetase levels and/or activity may be, for example, determined by measuring levels of glutamine, levels of glutamate, and/or determining the ratio between levels of glutamine and levels of glutamate, in a subject. The increase may be normal or healthy levels, where for example fatty liver disease is accompanied by a reduction in UCE. It will be appreciated that normal or healthy levels of glutamine and/or glutamate may vary depending on the sample in which these are measured. It will also be appreciated that normal or healthy levels of glutamine and/or glutamate may be subject specific, and depend on factors such as the subject's weight, diet, sex and age. Normal or healthy levels of glutamine and/or glutamate will be known to those skilled in the art.

As used herein, "amelioration" refers to the lessening of severity of at least one indicator or symptom of a condition or disease. In certain embodiments, amelioration includes a delay or slowing in the progression of one or more indicators of a condition or disease. The severity of indicators may be determined by subjective or objective measures, which are known to those skilled in the art.

As used herein the term "associated with" when used in the context of a disease or condition "associated with" the fat deposits in the liver means that the disease or condition may result from, result in, be characterised by, or otherwise associated with the elevated levels of ammonia. Thus, the association between the disease or condition and the fatty liver may be direct or indirect and may be temporally separated.

By the same token, appropriate samples for determination of glutamine synthetase levels and/or glutamine synthetase activity, include any appropriate or desired sample in which glutamine synthetase, glutamine and/or glutamate may be present. These may be any appropriate or desired tissue or body fluid sample. An example of a suitable tissue is liver and/or muscle tissue. Conveniently, a sample may be any body fluid sample, and typically will be blood or any blood-derived sample e.g. plasma or serum etc, but it may be any other body fluid e.g. urine, cerebrospinal fluid, or a stool or tissue sample etc, for example a biopsy sample or a lavage or washing fluid sample etc. This may depend of course on the precise nature of the condition to be treated etc.

As used herein the term “effective amount” includes within its meaning a non-toxic but sufficient amount or dose of, depending on the context, GS and/or an ammonia lowering agent, to provide the desired effect. It will be appreciated that the effective amount of the protein and/or the ammonia lowering agent may be different. Exemplary therapeutically effective amounts are specified elsewhere in this specification.

The exact amount or dose required will vary from subject to subject depending on factors such as the species being treated, the age and general condition of the subject, the severity of the condition being treated, the particular GS being administered and the mode of administration and so forth. Thus, it is not appropriate to specify an exact “effective amount”. However, for any given case, an appropriate “effective amount” may be determined by one of ordinary skill in the art using only routine experimentation.

Indeed, a surprising feature of the present invention is that contrary to the reports in the literature of a 5 or 10-subunit multimer, human GS may be expressed and/or obtained as a mixture of multiple different types of multimer, including also a monomeric form. The monomeric form has been shown to be active. Thus, according to the present invention, the GS may be used as a monomer and/or as a multimer, and the multimer may be provided as a single multimeric form, or as a mixture of different multimeric forms which may or may not include the monomer. As reported in the examples below, 4 or more, e.g. 4 to 10, e.g. 5 to 8 multimeric forms may be obtained. The multimers may range in size from 2 to 20 subunits.

Examples below, to assess the ability of the GS polypeptide to catalyze the conversion of glutamate and ammonia to glutamine.

In some examples, the GS protein used according to the invention herein is recombinant GS produced using prokaryotic or eukaryotic expression systems well known in the art. Exemplary prokaryotic expression systems include, but are not limited to, *Escherichia coli* expression systems, and exemplary eukaryotic expression systems include, but are not limited to, yeast, insect cell and mammalian cell expression systems.

Nucleic acid encoding GS can be obtained by any suitable method, including, but not limited to, RT-PCR of liver RNA and synthetic nucleotide synthesis. Primers for amplification can be designed based on known GS sequences, such as that set forth above. Nucleic acid and amino acid sequences of GS are well known in the art and provided in freely-available databases, such as, for example, the National Center for Biotechnology Information (NCBI) Nucleotide (ncbi.nlm.nih.gov/nuccore) and Protein (ncbi.nlm.nih.gov/protein) databases.

Nucleic acid encoding the GS polypeptide, such as nucleic acid having a sequence set forth in SEQ ID NO. 3, can be cloned into an expression vector suitable for the expression system of choice. In some instances, the nucleic acid is codon-optimized for expression in a particular system. For example, the nucleic acid encoding the GS polypeptide can be codon-optimised for expression in *E. coli*. An exemplary codon-optimised nucleic acid encoding GS for expression in *E. coli* is set forth in SEQ ID NO 5, which encodes a GS polypeptide comprising a His-tag attached via a GGGGS linker (as set forth in SEQ ID NO. 4).

Typically the nucleic acid encoding GS is cloned into an expression vector, operably linked to regulatory sequences that facilitate expression of the heterologous nucleic acid molecule. Many expression vectors suitable for the expression of GS are available and known to those of skill in the art. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

GS polypeptides also can be expressed as protein fusions. For example, a fusion can be generated to add additional functionality to a polypeptide. Examples of fusion proteins include, but are not limited to, fusions containing GS and an affinity tag for purification (e.g. a his-tag e.g. his6, MYC, FLAG, HA or GST tag), a leader sequence (such as the pelB leader sequence), a sequence for directing protein secretion, or a protein for stabilising and/or solubilising GS (e.g. maltose-binding protein (MBP)), or a protein for increasing in vivo half-life (e.g. albumin or Fc domains, or fragments thereof).

Prokaryotes, especially *E. coli*, provide a system for producing large amounts of GS. Transformation of *E. coli* is a simple and rapid technique well known to those of skill in the art. Expression vectors for *E. coli* can contain inducible promoters that are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated λPL promoter.

In other examples, eukaryotic expression systems are used to produce the GS, such as baculovirus expression systems. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda, Pseudaletia unipuncta* (A7S) and *Danaus plexippus* (DpN1). For high level expression, the nucleotide sequence of the GS is fused immediately downstream of the polyhedrin initiation codon of the virus.

Yeasts such as *Saccharomyces cerevisiae, Schizosaccharomyces pombe, Yarrowia lipolytica, Kluyveromyces lactis*, and *Pichia pastoris* can also be used expression hosts for GS. Yeast can be transformed with episomal replicating vectors or by stable chromosomal integration by homologous recombination. Typically, inducible promoters, such as include GALL GALT, and GALS, are used to regulate gene expression. Yeast expression vectors often include a selectable marker such as LEU2, TRP1, HIS3, and URA3 for selection and maintenance of the transformed DNA.

Mammalian expression systems also can be used to express GS. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). Exemplary cell lines available for mammalian expression include, but are not limited to, mouse, rat, human, monkey, and chicken and hamster cells, such as BHK, 293-F, CHO, Balb/3T3, HeLa, MT2, mouse NSO (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells.

Following expression, GS can be purified using any method known to those of skill in the art including, but not limited to, SDS-PAGE, size fraction and size exclusion chromatography, ammonium sulfate precipitation, chelate chromatography, ionic exchange chromatography and affinity chromatography. Affinity purification techniques can be used to improve the efficiency and purity of the preparations. For example, antibodies and other molecules that bind GS can be used in affinity purification. As discussed above, expression constructs can be engineered to add an affinity tag such as a his, myc, FLAG or HA tag or GST moiety to GS, which can then be affinity purified with Ni-resin, myc antibody, HA antibody, FLAG antibody or glutathione resin, respectively. Suitably, a poly 9×his tag may be used. More suitably, a 6×his tag is used. Purity can be assessed by any method known in the art including gel electrophoresis and staining and spectrophotometric techniques, such as SDS page and Size Exclusion Chromatography (SEC).

For use according to the present invention, the affinity tag (e.g. his tag etc) may be removed, but this is not necessary, and the GS polypeptide may be used with the tag attached.

The tag or other fusion partner may be attached to the GS via a linker, which may be any suitable linker, according to principles well known in the art. Such a linker may typically and conveniently be a short (e.g. 2 to 10, 2 to 8 or 2-6 mer) peptide. By way of example the linker GGSG, GGGS or GGGGS may be mentioned, but could be made up of any suitable amino acids. Amino acid linkers enable preparation of the fusion protein by recombinant means but non-amino acid-based linkers might also be used, again according to principles and techniques well known in the art and described in the literature. The linker may be cleavable (e.g. enzymatically) or non-cleavable.

GS polypeptides can be prepared as naked polypeptide chains or as modified polypeptides which are modified by coupling or conjugating to a further moiety or chemical group or substance. Exemplary modifications include, but are not limited to, pegylation, albumination or other known modifications. For example, in some instances, the GS polypeptides for use in the described methods are peglyated using standard methods well known in the art. This may serve, for example, to improve the half-life of the GS protein in the circulation. Thus, in a preferred embodiment of the invention the GS protein may be provided as a conjugate with a polymer such as polyethylene glycol (PEG) or a poly- or oligosaccharide. Conjugates with PEG are particularly preferred. As indicated above the preparation of such conjugates is well known in the art and described in the literature. Thus, PEGs of various sizes may be used to prepare the conjugates e.g. ranging from 100 Daltons to 100 kD, but more often from 5 kD to 100 kD, for example 12 or 15 kD to 60 or 80 kD, such as 15 to 50, 15 to 40, or 15 to 30 kD. Further, the PEG may be attached or linked to the GS protein in various ways, and more than one PEG may be attached to each single protein. It may be linked directly or indirectly, e.g. via a linker as described, for fusion proteins above or by any molecular or chemical group which may provide a linker function. Thus, the PEG may be linked at one or both of the N- or C-termini, or internally in the GS molecule, for example at the amino group of one or more lysine residues in the GS protein molecule or at any other chemical moiety or residue in the protein molecule. Methods for coupling or conjugating polymers such as PEG to proteins are well known in the art and described in the literature (see for example Roberts et al. 2012, Advanced Drug Delivery Reviews, 64 (supplement) 116-127 and Veronese 2001, Biomaterials 22, 405-417). The data presented in the Examples below shows that PEG conjugates prepared by linking the PEG to the N-terminal are especially effective, for example in activity assays of liver lysates from animals administered various conjugates. Accordingly, a PEG conjugate comprising a PEG linked to the N terminus of a GS protein represents one preferred embodiment of the present invention. The GS protein may be pegylated in monomeric and/or multimeric form. Thus, for convenience a preparation comprising both monomeric and various multimeric forms of GS may be subjected to pegylation.

GS can be formulated as a pharmaceutical composition for administration to a subject. GS can be formulated in any conventional manner by mixing a selected amount of GS with one or more physiologically or pharmaceutically acceptable carriers or excipients.

Accordingly, a further aspect of the invention provides a pharmaceutical composition comprising GS and one or more pharmaceutically-acceptable carriers or excipients, wherein the composition is for the treatment of fatty liver disease by reducing fat deposits in the liver. GS may be provided as a nucleic acid molecule, or a protein, as described herein.

Selection of the carrier or excipient is within the skill of the administering profession and can depend upon a number of parameters, such as the mode of administration. In some examples the GS protein is provided as a fluid. In other instances, the GS protein is provided in dried form, such as desiccated or freeze-dried form. Such dried forms can be rehydrated prior to administration by the addition of a suitable solution, such as water, buffer, saline or other suitable solution. Where GS is provided as a nucleic acid, it may be provided in any suitable composition, and may be an injectable for administration directly to the liver. GS provided herein can be formulated for direct administration or can be formulated for dilution or other modification. Accordingly, GS can be formulated in single (or unit) dosage forms or multiple dosage forms. Examples of single dose forms include ampoules and syringes. Examples of multiple dose forms include vials and bottles that contain multiple unit doses.

The concentrations of GS in the formulations are effective for delivery of an amount of GS that, upon administration, is effective to reduce or eliminate fat deposits in the liver so that the liver appears normal or healthy, at least in terms of the absence or substantial absence of fat within the liver cells. The concentrations and amounts of GS will depend on several factors, including the levels of the substrates in the subject, and mode of administration, and can be empirically determined. Exemplary concentrations of GS in the compositions provided herein include, but are not limited to, concentrations of or about 0.1, 0.5, 0.6, 0.7, 0.8, 0.9, 1, 5, 10, 15, 20, 30, 40, 50, 60, 70, 80, 90, 100, 200, 300, 400, 500, 1000, 2000, 3000, 4000 or 5000 mg/mL GS or more.

To formulate the GS composition, in one embodiment the weight fraction of GS is dissolved, suspended, dispersed, or otherwise mixed in a selected vehicle at the desired concentration. The resulting mixtures are solutions, suspensions, emulsions and other such mixtures, and can be formulated as a non-aqueous or aqueous mixture, including but not limited to, a solution, suspension, paste, gel, aerosol, spray, or any other formulation suitable for systemic administration.

Generally, the GS composition is prepared in view of approval from a regulatory agency or otherwise prepared in accordance with generally recognized pharmacopeia for use in animals and in humans. The GS composition can include carriers such as a diluent, excipient, or vehicle. Such pharmaceutical carriers can be sterile liquids, such as water and oils. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A GS composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents. Examples of suitable pharmaceutical carriers are described in "Remington's Pharmaceutical Sciences" by E. W. Martin.

Liposomal suspensions, including tissue-targeted liposomes, can also be suitable as pharmaceutically acceptable carriers. These can be prepared according to methods known to those skilled in the art. Liposomal delivery can also include slow release formulations, including pharmaceutical matrices such as collagen gels and liposomes modified with fibronectin.

As well as in pharmaceutical compositions, GS may also be formulated or administered in other ways, for example in a nutritional composition such as a dietary supplement, for example a parenteral nutrition composition (e.g. alone or alongside other supplement ingredients). Suitably, the nutritional supplement may be provided in a dosage regimen such that sufficient GS reaches the gut in order to have a detoxifying effect on ammonia. It may be included in such foods as a polypeptide (e.g. purified enzyme) or as part of an expressing host cell or organism. Thus for example microbial (e.g. yeast or bacterial or fungal) host cells or plants (including plants cells) may be engineered to express GS and may be administered as such, e.g. a whole cells or extracts or other processed products (in which enzymatic activity may be retained), or may be incorporated into nutritional compositions. Thus, for example, bacterial or yeast cells suitable for human or non-human animal consumption may be engineered to express GS (namely by introduction of a nucleic acid molecule comprising a nucleotide sequence encoding GS). Alternatively, plants may be engineered in an analagous manner and appropriate plant parts etc (e.g. seeds, leaves, tubers etc) may be provided for administration. It is known in the art which microorganisms (yeasts, bacteria, algae or fungi for example) are suitable for human or other animal consumption and many such organisms are used today, for example in probiotic formulations. Any such probiotic organisms or formulations could be used e.g. based on lactic acid bacteria such as *Bifidobacterium* or *Lactobacillus* sp. (e.g. *L. acidophilus*) etc. Thus, according to the present invention such organisms or preparations may be formulated for and administered directly into the GI tract, e.g. by injection or infusion, or enema or rectal administration etc. The precise amount or dose of the GS administered to the subject depends on the activity of the GS, the route of administration, the disease or condition being treated, the number of dosages administered, and other considerations, such as the weight, age and general state of the subject. Particular dosages and administration protocols can be empirically determined or extrapolated from, for example, studies in animal models. Exemplary therapeutically effective doses of the GS include, but are not limited to, from or from about 0.1 mg/kg body weight per day to or to about 10000 mg/kg body weight per day, including from or from about 1 mg/kg to or to about 1000 mg/kg body weight per day, or from or from about 10 mg/kg to or to about 100 mg/kg body weight per day Thus, for example, a subject can be administered 0.1, 0.2, 0.3, 0.4, 0.5, 1, 5, 10, 20, 30, 40, 50, 60, 70, 80, 90, 100, 200, 400, 600, 800, 1000, 2000, 4000, 6000, 8000, 10000, or 20000 mg or more the GS per kg body weight per day.

It is a feature of the present invention that the GS is administered systemically. Accordingly GS can be administered by any method and route that delivers GS systemically to the body. In certain embodiments GS may be administered parenterally. A skilled artisan would readily understand and be able to select appropriate modes of administration or delivery, including, but not limited to, intravenous, intramuscular, intradermal, transdermal, subcutaneous, or intraperitoneal administration, as well as by any combination of any two or more thereof, formulated in a manner suitable for each route of administration. In some instances, GS, or a GS composition or product as described herein may be administered subcutaneously. In other instances GS, or a GS composition or product as described herein may be administered intravenously. For example, the GS compositions can be administered intravenously by injection or infusion, such as by an intravenous bolus.

Systemic administration may be oral. By oral administration is meant per-oral delivery. Accordingly, non-oral means that GS is not administered by ingestion via the mouth. Other means of administration which deliver the GS protein to the intestines or more generally the gastrointestinal (GI) tract may be included (e.g rectally, or by enema, or direct administration into the GI tract). In a further embodiment the invention does not include administration to the muscle, particularly to skeletal muscle. Thus, in such an embodiment the administration is not directed to muscle, i.e. is a non-muscle directed therapy.

GS may also be administered in conjunction or combination with other therapeutic or active agents, notably a second or further therapeutic agent which may treat (e.g. to improve) fatty liver disease. The second or further agent typically be an ammonia lowering agent such as a nitrogen scavenger (or an ammonia scavenger) or a replacement amino acid or urea cycle intermediate, or an analogue thereof. Such an agent may therefore include an amino acid, for example arginine, glutamate, citrulline and/or ornithine, and/or N-acetyl glutamate and/or the analogue molecule carbamyl glutamate (Carbaglu®). More suitably, the second or further agent is an ammonia lowering agent, more suitably a nitrogen scavenger. Such an embodiment gives rise to certain aspects of the present invention.

The term "ammonia lowering agent" refers to a compound which removes ammonia e.g. from the blood of a subject being treated and/or reduces, or inhibits ammonia production. An ammonia lowering agent may also be referred to as an ammonia scavenger. An ammonia lowering agent may be an agent which reduces blood concentration of ammonia. An ammonia lowering agent may be an agent or compound which increases excretion of ammonia or reduces its production in a subject. Excretion of ammonia may be increased by providing compounds which bind to ammonia, and is excreted. An ammonia lowering agent may be a small molecule. An ammonia lowering agent may be selected from the group consisting of a nitrogen scavenger, an ion exchange resin (for example Relypsa), an ammonia absorber (such a liposomal based ammonia absorber, for example Versantis), an engineered microbiome that removes ammonia (for example Synlogic), Rifaximin and Lactulose.

The term "nitrogen scavenger" as used herein, refers to a compound or agent which reduces the levels of nitrogen and/or ammonia in a subject by removing ammonia. Suitably, a nitrogen scavenger lowers the blood concentration of ammonia. The terms ammonia scavenger and nitrogen scavenger are understood by a person skilled in the art. In a suitable embodiment the nitrogen scavenger reduces the amount of nitrogen and/or ammonia (suitably the blood concentration) in the subject by being metabolised to phenylacetyl glutamine, which may be then excreted in urine.

In a suitable embodiment, a nitrogen scavenger may be selected from the group consisting of a pharmaceutically acceptable salt of phenylacetic acid (also referred to herein as phenylacetate), a pharmaceutically acceptable salt of phenylbutyric acid (also referred to herein as phenylbutyrate), glycerol phenylbutyrate, a pharmaceutically acceptable salt of benzoic acid, a pharmaceutically acceptable pro-drug thereof, and ammonia binding resin. Other nitrogen scavengers will be well known to those skilled in the art.

As used herein, the term "pharmaceutically-acceptable salt" includes, for example, an acid-addition salt of phenylacetic acid which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of phenylacetic acid which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl) amine.

In a suitable embodiment, a pharmaceutically acceptable salt of phenylacetic acid may be selected from the group consisting of sodium phenylacetate, potassium phenylacetate, ornithine phenylacetate.

In a suitable embodiment, a pharmaceutically acceptable salt of phenylbutyric acid may be selected from the group consisting of sodium phenylbutyrate and potassium phenylacetate.

In a suitable embodiment, a pharmaceutically acceptable salt of benzoic acid may be selected from the group consisting of sodium benzoate and potassium benzoate.

It shall be understood that an ammonia lowering agent may exist in solvated as well as unsolvated forms such as, for example, hydrated forms. It is to be understood that in the context of the present invention encompassed are all such solvated and unsolvated forms.

The term "pro-drug" as used herein refers to an agent rendered less active by a chemical or biological moiety than the ammonia lowering agent (such as nitrogen scavenger), but which metabolises into or undergoes in vivo hydrolysis to form the ammonia lowering agent.

In particular, agents such as phenylacetate or phenylbutyrate compounds are preferred, which act to remove glutamine from the circulation (glutamine being formed by the action of GS). The second or further agent, such as an ammonia lowering agent, may be administered separately, sequentially or simultaneously with the GS protein, including in the same formulation or composition, or in a separate composition or formulation.

A second or further agent may be administered by the same administration route or by a different administration route, including orally. Thus, in one exemplary embodiment the second or further, such as an ammonia lowering agent, agent may be administered orally, or by other systemic means and the GS may be administered by non-oral systemic means.

Ammonia lowering agents, such as nitrogen scavengers (including sodium phenylacetate, ornithine phenylacetate, sodium phenyl butyrate, or sodium benzoate) may be administered by intravenous infusion e.g. for acute management, and/or orally, e.g for long-term maintenance. The i.v. infusion may be peripheral but central i.v. infusion is preferred. Similarly amino acids such as arginine may be administered orally or i.v., for example by central i.v. infusion.

Such kits may be provided for use in treating fatty liver disease. The components of the kit may be provided as separate pharmaceutical compositions comprising the agent (s) in question together with one or more pharmaceutically-acceptable carriers or excipients. The composition(s) of the invention can be administered once or more than once. If the composition(s) are administered more than one time, they can be administered at regular intervals or as needed, for example as determined by a clinician. Regular intervals can include, for example, approximately daily, weekly, bi-weekly, monthly, or any other interval. Selecting a treatment protocol is well within the level of skill of the skilled artisan. For example, a protocol can be determined based upon studies in animal models. In other example, repeat doses of the composition(s) can be administered to a subject if the ammonia level in the blood, is above a predetermined level.

The use of the GS protein, or the use of the ammonia lowering agent in combination with a GS protein, according to the present invention is advantageous for the treatment of subjects for whom gene therapy is not suitable or appropriate, for example children or subjects who are refractory to gene therapy. Such refractory subjects may include for example those who have previously been exposed to, or have had an immune reaction to, the viral vector used for delivery of the gene therapy.

Advantageously, the use of a protein as the therapeutic agent allows higher doses of the active protein to be delivered to the subject and for doses to be adjusted according to subject and to need. Furthermore, as compared to gene therapy, protein therapy allows for a much faster response, and hence is more suitable for emergency use.

As mentioned, one aspect of the invention relates to a pharmaceutical composition comprising an ammonia lowering agent, for use in combination with GS protein for use in treating fatty liver disease. The ammonia lowering agent can be formulated as a pharmaceutical composition for administration to a subject. The ammonia lowering agent, can be formulated in any conventional manner by mixing a selected amount of the nitrogen scavenger, with one or more physiologically or pharmaceutically acceptable carriers or excipients. Suitably, the composition may be for non-oral systemic administration, or oral administration. It will be appreciated that the pharmaceutical composition may also comprise GS protein. In such an embodiment, the composition will be formulated for non-oral systemic administration.

Selection of the carrier or excipient is within the skill of the administering profession and can depend upon a number of parameters, such as the mode of administration. In some examples the ammonia lowering agent, is provided as a fluid. In other instances, the ammonia lowering agent, is provided in dried form. Such a dried form can be rehydrated prior to administration by the addition of a suitable solution, such as water, buffer, saline or other suitable solution. The ammonia lowering agent can be formulated for direct administration or can be formulated for dilution or other modification. Accordingly, the ammonia lowering agent can be formulated in single (or unit) dosage forms or multiple dosage forms. Examples of single dose forms include ampoules and syringes. Examples of multiple dose forms include vials and bottles that contain multiple unit doses.

The concentration of the ammonia lowering agent in the formulations are effective for delivery of an amount of ammonia lowering agent that, upon administration, is effective to remove nitrogen and/or ammonium from the circulation, or reduce or inhibit ammonia production. The concentrations and amounts will depend on several factors, including the levels of the substrates in the subject, and mode of administration, and can be empirically determined. Exemplary concentrations of the ammonia lowering agent in the compositions provided herein include, but are not limited to, concentrations of or about 0.1, 0.5, 0.6, 0.7, 0.8, 0.9, 1, 5, 10, 15, 20, 30, 40, 50, 60, 70, 80, 90, 100, 200, 300, 400, 500, 1000, 2000, 3000, 4000 or 5000 mg/mL of ammonia lowering agent or more.

To formulate the ammonia lowering agent composition, in one embodiment the weight fraction the ammonia lowering agent is dissolved, suspended, dispersed, or otherwise mixed in a selected vehicle at the desired concentration. The resulting mixtures are solutions, suspensions, emulsions and other such mixtures, and can be formulated as a non-aqueous or aqueous mixture, including but not limited to, a solution, suspension, paste, gel, aerosol, spray, or any other formulation suitable for systemic administration.

Generally, the ammonia lowering agent is prepared in view of approval from a regulatory agency or otherwise prepared in accordance with generally recognized pharmacopeia for use in animals and in humans. The composition can include carriers such as a diluent, excipient, or vehicle. Such pharmaceutical carriers can be sterile liquids, such as water and oils. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A phenylacetic acid, or a pharmaceutically acceptable salt thereof composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents. Other examples of suitable pharmaceutical carriers will be known to those skilled in the art.

The ammonia lowering agent can be administered by any method and route that delivers the compound to the body. In certain embodiments, the ammonia lowering agent can be administered parenterally. A skilled artisan would readily understand and be able to select appropriate modes of administration or delivery, including, but not limited to, oral, intravenous, intramuscular, intradermal, transdermal, subcutaneous, or intraperitoneal administration, as well as by any combination of any two or more thereof, formulated in a manner suitable for each route of administration.

As well as in pharmaceutical compositions, the ammonia lowering agent may also be formulated or administered in other ways, for example in a nutritional composition such as a dietary supplement, for example a parenteral nutrition composition (e.g. alone or alongside other supplement ingredients). Suitably, such a composition may be for oral or non-oral administration.

As mentioned, the ammonia lowering agent is for administration in combination with GS. It will be appreciated that the ammonia lowering agent may be administered separately, sequentially or simultaneously with GS, including in the same formulation or composition, or in a separate composition or formulation. Thus, in one exemplary embodiment the ammonia lowering agent may be administered orally, or by other systemic means and GS may be administered by non-oral systemic means.

Exemplary therapeutically effective doses of the ammonia lowering agent, include but are not limited to, from about 1 mg/kg body weight per day to or to about 2000 mg/kg body weight per day, including from or from about 10 mg/kg to or to about 1000 mg/kg body weight per day, or from or from about 100 mg/kg to or to about 500 mg/kg body weight per day. Thus, for example, a subject can be administered 1, 2, 3, 4, 5, 10, 20, 30, 40, 50, 60, 70, 80, 90, 100, 150, 200, 250, 300, 350, 400, 450, 500, 550, 600, 650, 700, 750, 800, 850, 900, 950, 1000, or 2000 mg or more of the ammonia lowering agent per kg body weight per day. Other exemplary therapeutically effective doses of the ammonia lowering agent, include but are not limited to, from about 1 g/day to about 50 g/day. Thus, for example, a subject can be administered 1, 2, 3, 4, 5, 10, 20, 30, 40, or 50 grams, or more of the ammonia lowering agent per day. It will be appreciated that the effective dose may vary depending on the ammonia lowering agent. The GS composition, and/or the composition comprising the ammonia lowering agent or composition comprising a further agent which is not an ammonia lowering agent, if desired, can be presented in a package, in a kit or dispenser device, such as a syringe with a needle, or a vial and a syringe with a needle, which can contain one or more unit dosage forms. The kit or dispenser device can be accompanied by instructions for administration. In an embodiment where the GS composition and the composition comprising the ammonia lowering agent are separate, the kit may comprise the GS composition and the composition comprising the ammonia lowering agent. Suitably, in such an embodiment, the kit may comprise a GS composition, and a nitrogen scavenger. Suitably, in such an embodiment, the kit may comprise a GS composition, and a composition comprising phenylacetate, for example sodium phenylacetate. The compositions can be packaged as articles of manufacture containing packaging material, the composition, and a label that indicates that the composition is for administration to subjects for the treatment of fatty liver disease or a disease or condition associated with fatty liver disease.

Suitable systemic administration methods will be known to those skilled in the art. By way of example, systemic administration may be achieved by parenteral route of administration, such as intravenous or subcutaneous route. It will be appreciated that "systemic administration" allowed the product (such as glutamine synthetase or a biologically fragment thereof) of an expression vector to be expressed within multiple sites in the patient. In the context of the present invention, systemic administration does not include intramuscular administration.

It will be appreciated that (except where the context requires otherwise), described with reference to GS for use in treating fatty over disease, GS protein for use in combination with an ammonia lowering agent, ammonia lowering agent for use in combination with GS, their uses, methods of treatment, compositions, kit and product, will generally be applicable, to the remaining aspects of the invention.

BRIEF DESCRIPTION OF THE DRAWINGS

The present invention will now be further described with reference to the following non-limiting Examples and Figures in which.

EXAMPLES

Example 1

Production and Purification of GS Protein and GS Protein-PEG Conjugates

Production of human glutamine synthetase (GS): pET30a+ vector, containing the gene for human GS (SEQ ID NO. 5 comprising a 5' sequence encoding a His-tag and the linker GGGGS at the N-terminal end of the GS and codon optimised for expression in bacteria) was used in an *E. coli* expression system. After plasmid construction, evaluation for the expression of GS was performed with a wide range of induction (IPTG) and expression temperatures. Human GS was solubly expressed in the construct as detected by SDS-PAGE. Lysis buffer (50 mM Tris pH 8.0, 10% glycerol, 0.1% Triton X-100, 100 ug/ml lysozyme, 1 mM PMSF, 3 Units DNAse, 2 mM MgCl) was used to extract soluble protein from cells. Soluble protein was extracted following centrifugation. After expression studies, the best condition found with BL21 (DE3) cells, cultured and induced with 0.1 mM IPTG at 25° C. for 16 hours. Other conditions tried, included using varied IPTG induction (from 0.01M-0.1M IPTG), various incubation temperatures (ranging from 16° C.-37°), and induction incubation times from 4-16 hours.

Purification of the expressed GS: the first step purification of the expressed protein comprised His tag purification with Ni-NTA beads, washing with 20 mM Imidazole, and elution with 300 mM Imidazole.

Protein PEG conjugation: the GS protein was conjugated under reducing conditions (with the use of 20 mM Sodium Cyano borohydride) to N-terminal aldehyde 20 kDa peg for 16 hours (Dr Reddy's 20 kDa N-terminal Aldehyde PEG).

Figure 1:
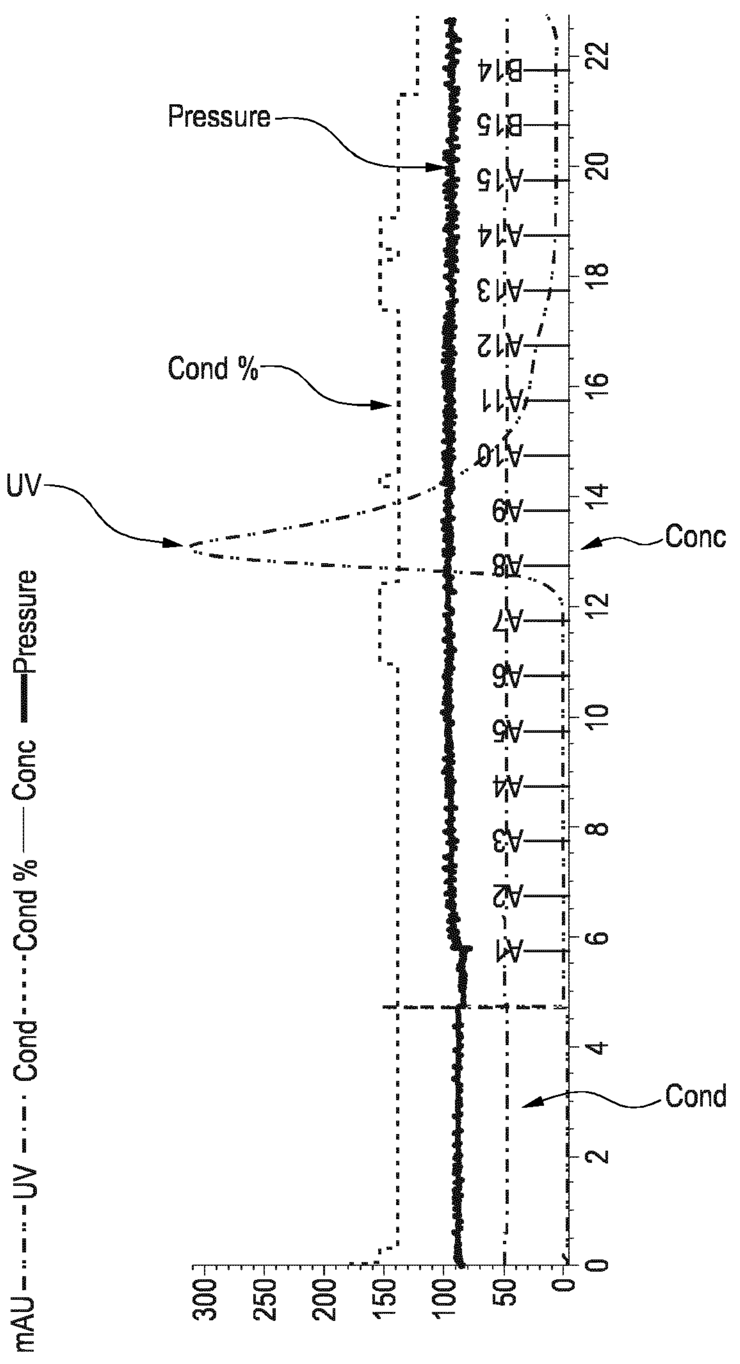
FIG. 1 shows the results of size exclusion chromatography (SEC) on a Superose 12 column of 20 kDa N-terminal aldehyde PEG conjugates of human GS protein as prepared in Example 1. The graph shows that multimers were eluted in fractions 8 and 9, and monomer in fraction 10.

Final purification: Conjugated protein was further purified using SEC chromatography. A Superose 6 or Superose 12 column (see FIG. 1) was used. Multimers were found in fractions 8+9. Fraction 10 in Superose 12 comprised (dilute) multimer. In Superose 6, multimers were found in fractions 8+9 and monomer in fractions 12/13.

A final formulation of the GS in PBS, pH 7.4 containing trehalose and sucrose was prepared.

Example 2

Activity of GS Preparations

Various GS preparations and PEG conjugates prepared according to Example 1 were tested for GS activity using the assay of Acosta et al., 2009 (supra), modified from the original assay described in Ehrenfeld et al., 1963, J. Biol. Chem. 238(11), 3711-3716.

Figure 2:
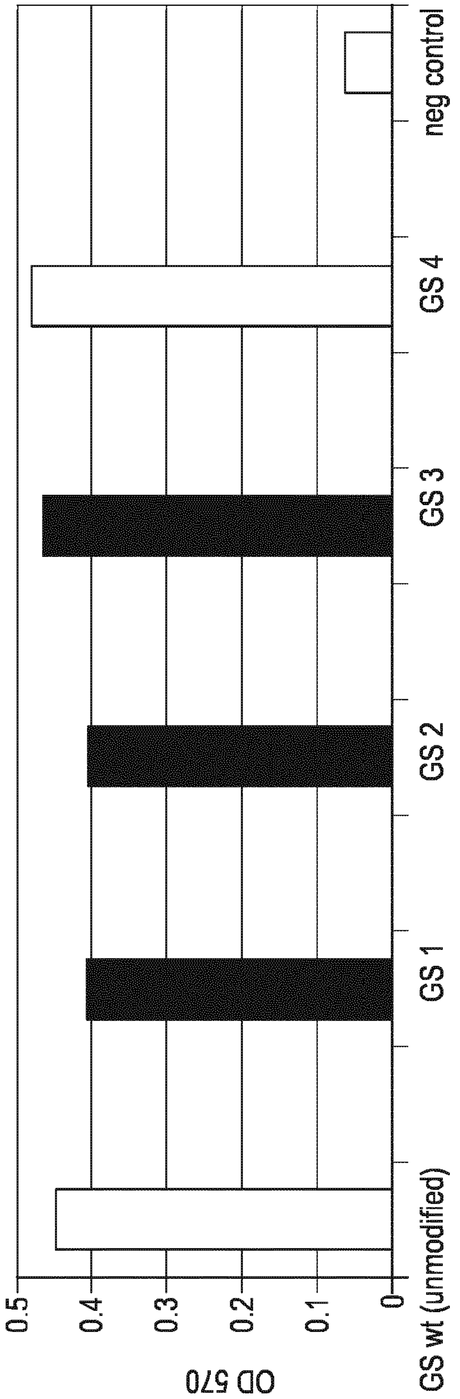
FIG. 2 shows a comparison of the in-vitro GS activity of various GS candidates: PEG-conjugated variants (GS1, GS2, GS3, GS4) versus non-conjugated GS (wt GS) and negative control. Glutamine Synthetase activity is shown as OD 570 nm according to the assay of Acosta et al, 2009, World J. Gastroenterol., 15(23), 2893-2899. GS1—(N-term Aldehyde monomer); GS2—Nof-20™; GS3—Nof-30™, GS4—N-term Aldehyde multimer.

100 ug of purified protein sample was added to the following reaction buffer: 150 μL stock solution (100 mmol/L imidazole-HCl buffer [pH7.1], 40 mmol/L $MgCl_2$, 50 mmol/L, β-mercaptoethanol, 20 mmol/L ATP, 100 mmol/L, glutamate and 200 mmol/L hydroxylamine, adjusted to pH 7.2) Tubes were incubated at 37° C. for 15 min. The reaction was stopped by adding 0.6 mL [2× concentration] ferric chloride reagent (0.37 mol/L $FeCl_3$, 0.67 mol/L HCl and 0.20 mol/L trichloroacetic acid). Samples were placed for 5 minutes on ice. Precipitated proteins were removed by centrifugation at 10,000 g, and the absorbance of the supernatants was read at 535-570 nm against a reagent blank. The results are shown in FIG. 2. Trin1—(N-term Aldehyde monomer PEG of 20 kD size, obtained from Dr Reddy's); Trin2—Nof-20 conjugated GS, which was conjugated to the GS protein with a monofunctional linear 20 kD PEG, NHS active ester, obtained from NOF corporation); Trin 3—Nof-30, conjugated to the GS protein with a monofunctional linear 30 kD PEG, NHS active ester, obtained from NOF corporation) Trin4—N-term Ald, GS multimers). Trin 4 (N-term Ald multimer) showed the best activity, with a very similar activity profile compared to the wt GS (non-conjugated), though activity of other conjugates was similar.

Example 3

Figure 3:
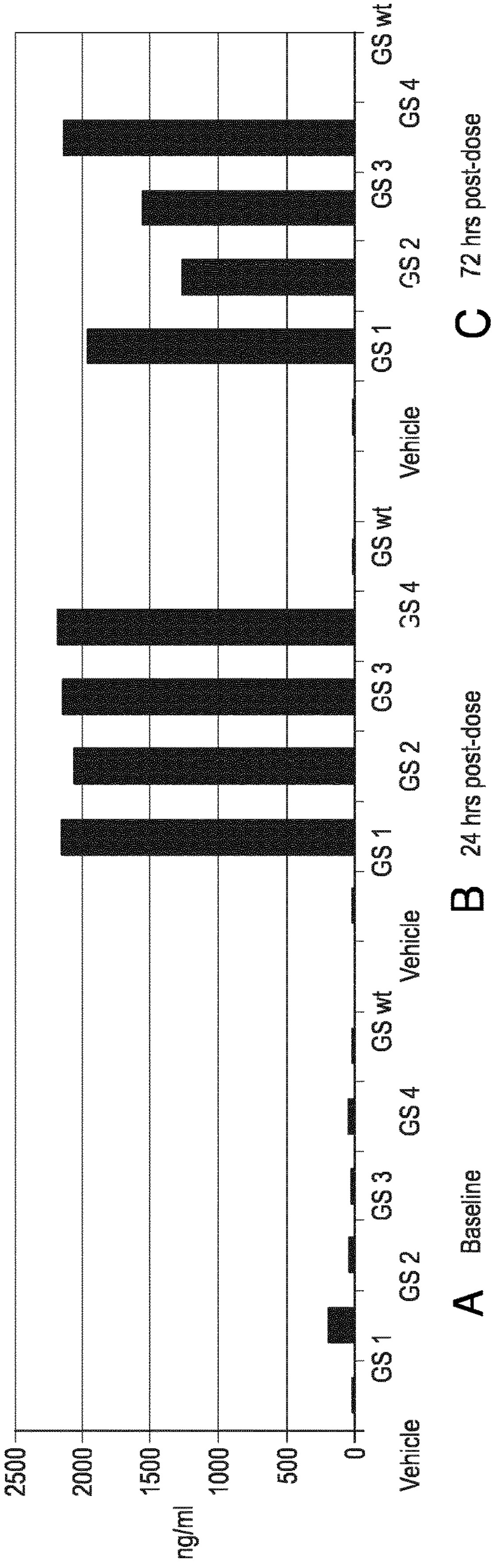
FIG. 3 shows PEG ELISA results on plasma pre- and post-dosing of male, wild-type (wt) CD1 mice of various conjugates at (A) baseline, (B) 24 hours post-dose and (C) 72 hours post-dose. (1—N-terminal Aldehyde conjugated GS monomer; 2—Nof20™ GS conjugated multimer; 3—Nof30™ conjugated GS multimer; 4—N-terminal Aldehyde conjugated PEG multimer)

Dosing of GS Protein to Mice—Effects on Plasma Levels of GS Protein-PEG Conjugates Male, wild-type (wt) CD1 mice were dosed at 2.5 mg/kg with subcutaneous (s.c) dosing of various GS protein and PEG conjugates prepared as described in Example 1 (Trin1—N-terminal Aldehyde conjugated GS monomer; Trin2—Nof-20 GS conjugated multimer; Trin 3—Nof-30 conjugated GS multimer; Trin4—N-terminal Aldehyde conjugated PEG multimer). The ELISA was conducted according to the protocol outlined by the manufacturer (Abcam PEG ELISA kit, ab133065). Results of the plasma ELISA, as shown in FIG. 3, show either very low or undetectable levels for unconjugated wt GS, as expected at all timepoints. After 24 hours, several candidates were found to be at a high level in plasma; however, after 72 hours post-dosing, Trin-GS 4 (N-terminal Aldehyde conjugated PEG GS multimer) showed the highest presence. N=2 animals in each group. Thus, this experiment shows that systemic administration of GS protein may be used successfully to obtain high circulating levels of the GS PEG conjugates, and in particular at levels which may be therapeutically effective or active.

Example 4

Dosing of GS Protein to Mice—GS Activity Levels of Liver Lysates

Figure 4:
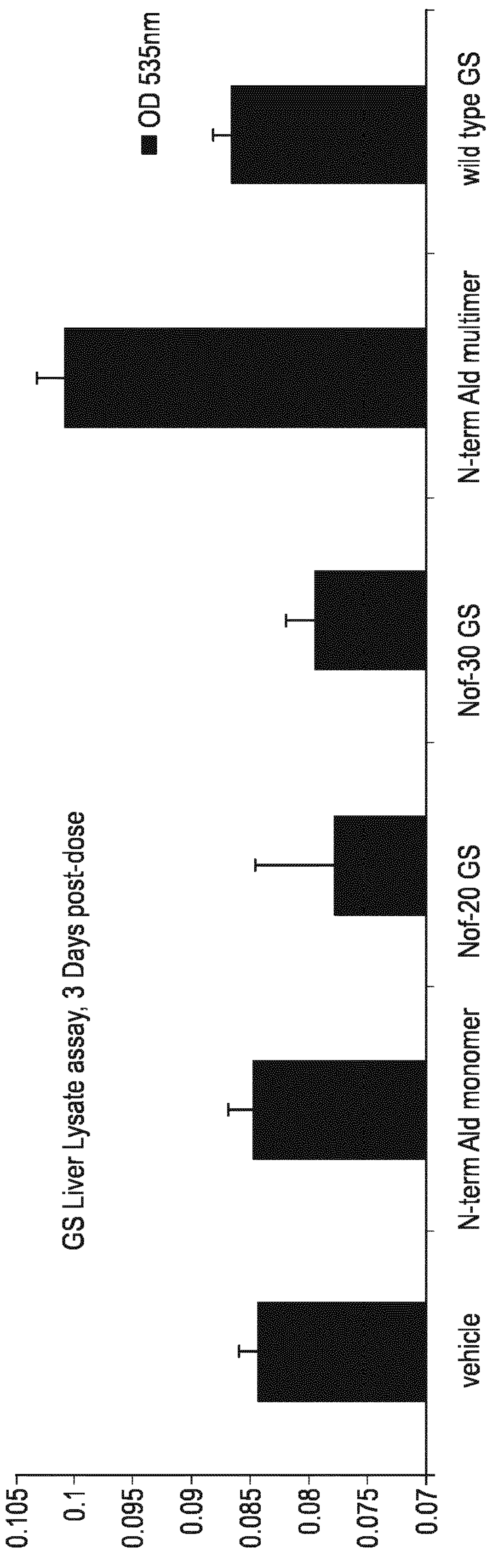
FIG. 4 shows GS activity (OD 535 nm) results in liver lysates in dosed wtCD1 mice at 2.5 mg/kg, 3 days post-dosing, as described in Example 3.

The activity assay was performed as described in Example 2, with the exception that 500 μg of liver lysate (from culled mice from the experiment of Example 3) was added to each reaction where appropriate. The results are shown in FIG. 4. The GS activity results in liver lysates 3 days post-dosing demonstrate that the superior candidate was the N-terminal aldehyde conjugated PEG GS multimer, which was the only candidate to show significant activity above baseline compared to the vehicle (saline-dosed) control. N=2 animals in each group.

Example 5

The $Otc^{spf\text{-}ash}$ Mouse model of urea cycle disorder (OTC deficiency) was used to show the effects of GS and GS+SP. The details of the mice used can be found at online on the publicly available website of the Jackson Laboratory (referencing strain #00181; B6EiC3Sn a/A-$Otc^{spf\text{-}ash}$/J). They are fed normal chow. The ages were variable from about 10 weeks to 23 weeks, with groups well-matched. All animals are male hemizygous (as OTC is X-linked, it is present only on the X chromosome of the males, therefore the mice are knockout).

Figure 6:
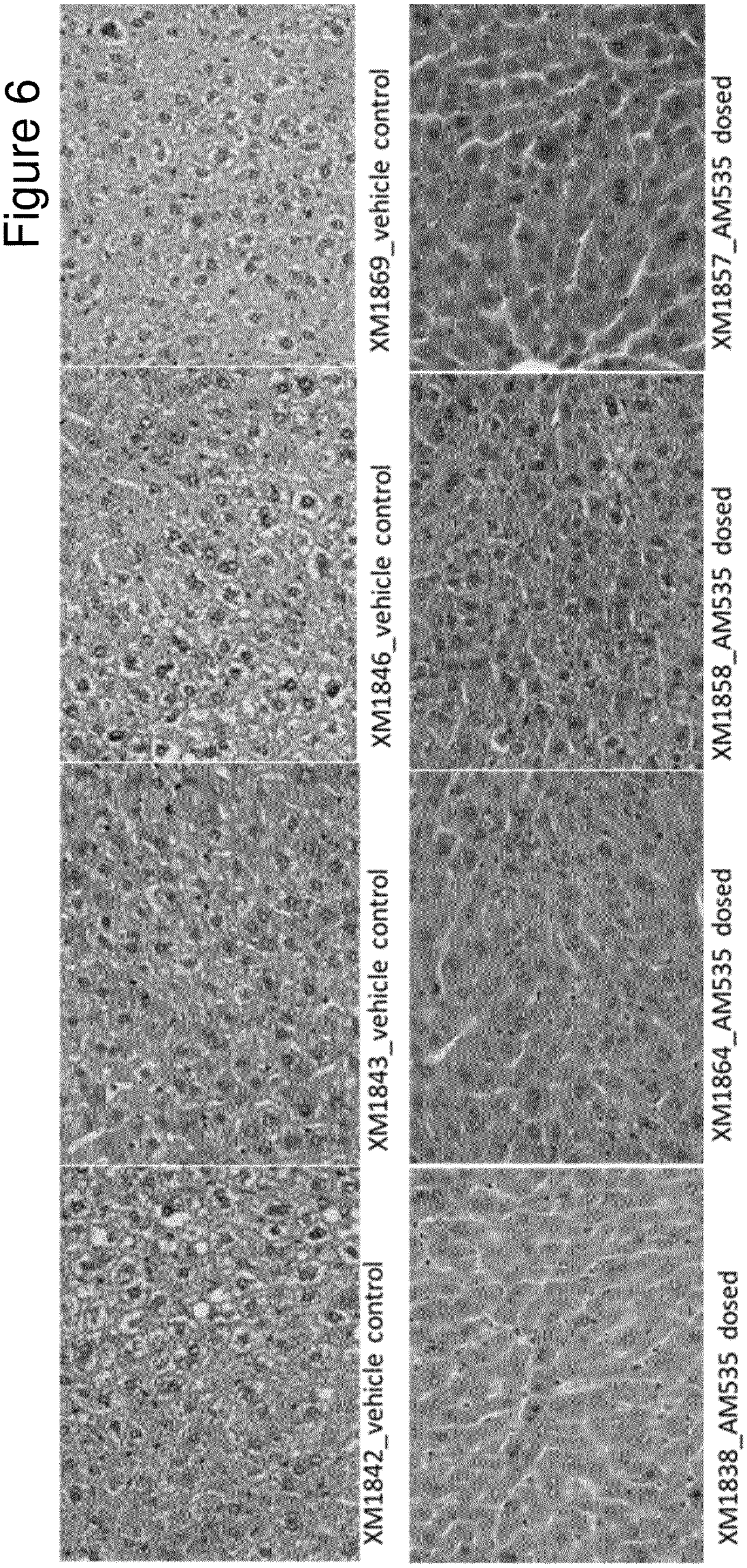
FIG. 6 shows the liver biopsies stained (with haematoxylin and eosin) of dosed and non-dosed OTC mice. Recombinant human GS protein dosed mice show normal liver architecture compared to non-dosed mice.

A non-peglyated human GS comprising an N terminal GGGS linker, and a GGGGS linker was used. This is referred to in FIG. 6 as A1V1535. All groups (vehicle, GS and GS+SP; where GS=Glutamine synthetase, GS+SP=Glutamine Synthetase+Sodium Phenlyacetate) were treated as follows:

The experiment ran from a Tuesday until the following Wednesday (8 days).

SP was dosed i.p. 350 mg/kg twice daily; GS was dosed in all treated groups for the first 4 days (i.p. @ 40 mg/kg once daily), then a break of 2 days [a weekend], and 3 more days of dosing with GS @ 40 mg/kg i.p.

Mice were culled on day 8, and blood extracted, spun down for plasma, and this plasma was used for ammonia quantitation (see method below).

Genotyping is performed using standard methods described in the literature.

Materials and Methods

All experiments were performed in accordance with the Animals (Scientific Procedures) Act of 1986, which was revised according to the European Directive2010/63/EU. All animals received humane care according to the criteria outlined in the Guide for the Care and Use of Laboratory Animals (National Institutes of Health publication 86-23; revised 1985). All the animals used in these experiments were Male Sprague-Dawley rats (body weight, 250 g at the beginning of the experiments) were obtained from Charles River Laboratories (Kent, UK) and divided into 5 groups: bile duct ligated animals+ammonia+saline serum (BDL+HA+SS, n=6), bile duct ligated animals+ammonia+sodium phenylacetate (BDL+HA+SP, n=6), bile duct ligated animals+ammonia+sodium phenylacetate+glutamine synthetase (BDL+HA+SP+GS, n=5), bile duct ligated animals+ammonia+glutamine synthetase (BDL+HA+GS, n=6), sham-operated animals+glutamine synthetase (SHAM+GS, n=5). Treatment comprising SP and GS may be referred to as "COMBO".

Bile Duct Ligation Surgery

Under general anesthesia (5% isoflurane in 100% oxygen for induction, 2% isofluorane in air for maintenance) rats underwent triple ligation of the bile duct (way of a small laparotomy) to induce chronic liver injury and were studied 28 days after surgery. A midline abdominal incision was made under anesthesia. In the BDL group, the common bile duct was isolated, triply ligated with 3-0 silk, and sectioned between the ligatures. The sham-operated group performed the same procedure without the sectioning between the ligatures. After BDL all animals continued to gain weight and were comparable with sham controls. The overall mortality in both groups was less than 10% and occurred within 36 hours of the operation.

Noncirrhotic Hyperammonemia Condition

Twenty-three rats were administered a hyperammonemic (HA) diet. The amino acid recipe used for a stock of approximately 100 g was: 15 g leucine, 7.7 g phenylalanine, 7 g glutamate, 10 g alanine, 4.4 g proline, 5.8 g threonine, 11 g aspartate, 5 g serine, 4.8 g glycine, 3.3 g arginine, 9.6 g lysine, 8.4 g histidine, 3 g tyrosine, 1.5 g tryptophan, and 10.6 g valine. 25 g of this mix (mixed 1:5 with standard rodent chow powder) was freshly prepared daily and rats were given free access to it for 5 days. The recipe approximates the amino acid composition of a rodent haemoglobin, [1] mimicking the effect of gastrointestinal bleeding, which is known to result in systemic hyperammonemia [2].

Sodium Phenylacetate Condition

Eleven rats were administered a sodium phenylacetate (SP) diet. 0.3 g/kg a day for 5 days was mixed with the chow powder and freshly prepared daily.

Glutamine Synthetase Condition

Sixteen rats were injected with GS intraperitoneally every two days (day 1 and day 3). The total volume injected was 3 mls i.p., which allows for 18-22 mg/kg of GS.

Results

Dosing of GS Protein to Mice—GS Activity Levels in Liver and Blood

Figure 5A:
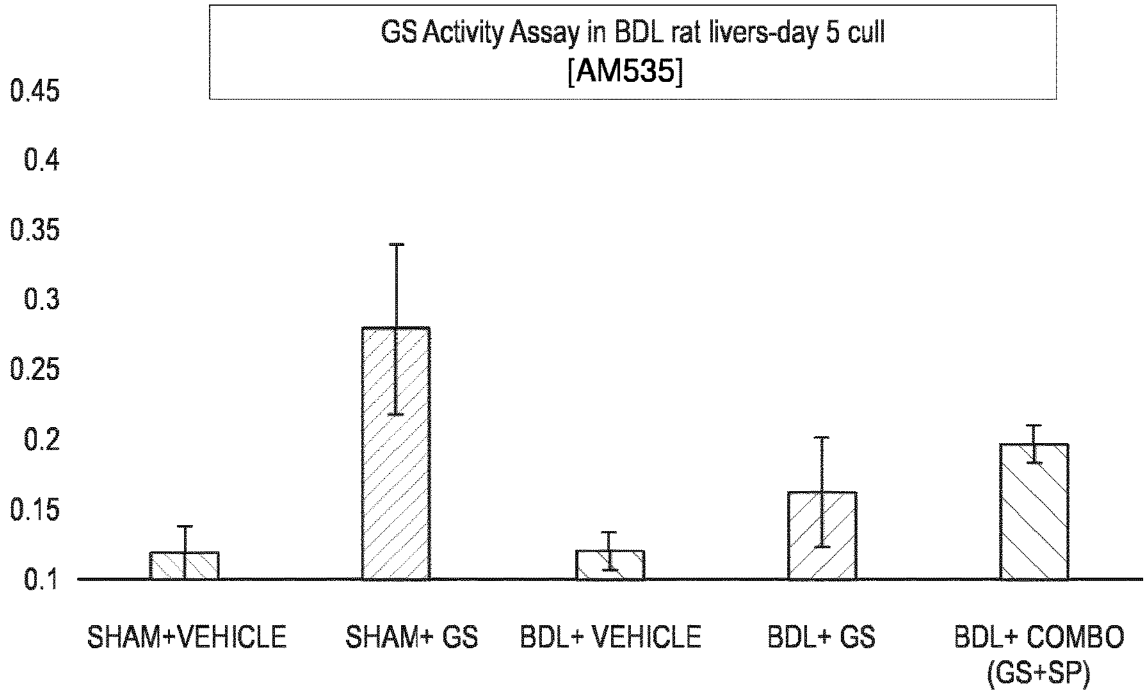
FIG. 5A shows liver GS activity assay results.
Figure 5B:
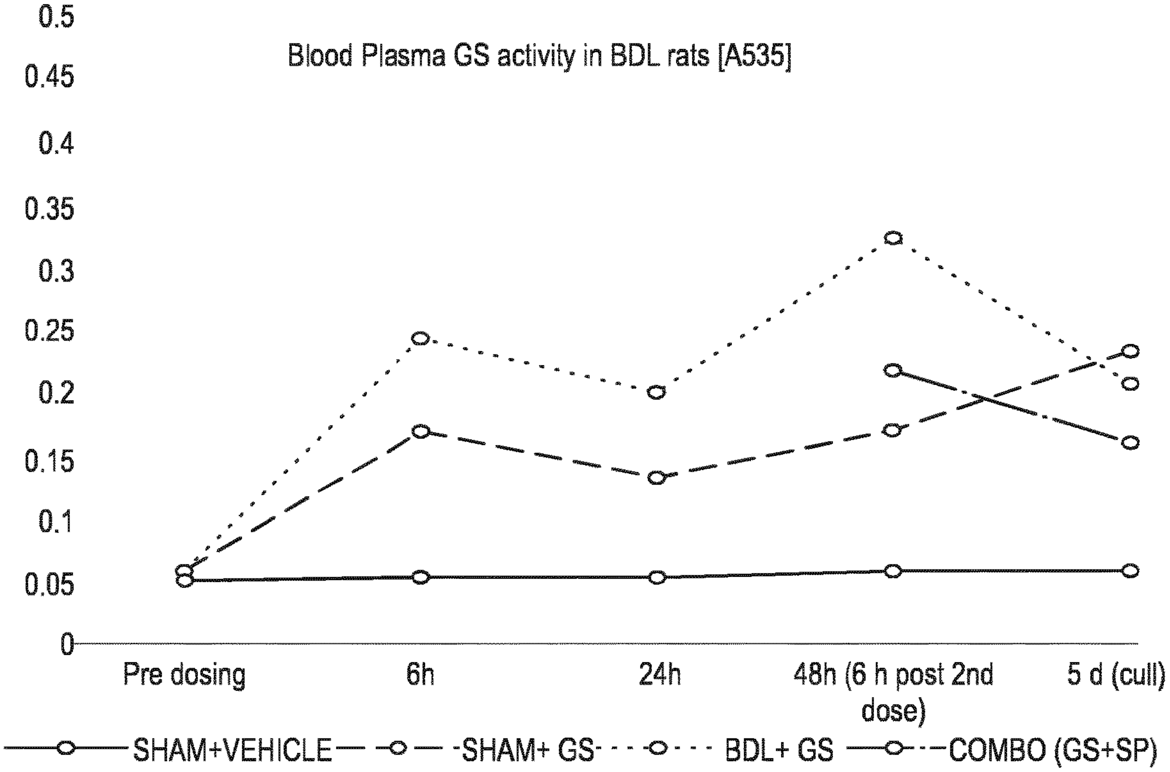
FIG. 5B shows blood plasma GS activity assay results. Both, liver and blood plasma GS activity was assayed in bile duct ligated (BDL) rats treated with GS protein, and GS protein with nitrogen scavenger.

The activity assay was performed as described in the materials and methods section above. The results are shown in FIGS. 5A and B. The results in rat liver measured at day 5, show that GS activity is best in the SHAM+GS group. Additionally, it can been seen from FIG. 5A that GS and GS+SP treatment increase GS activity in the livers of mice which have undergone BDL. When measured in blood, the results show that GS activity is best in the BDL+GS group. Additionally, from FIG. 5B, it can be seen that GS activity in blood is consistant over time, even 24 hrs and 48 hrs post dosing.

Hematoxylin and Eosin (H & E) Staining of OTC Mouse Livers

The staining method involves application of hemalum, which is a complex formed from aluminium ions and oxidized hematoxylin. This colours nuclei of cells blue. The nuclear staining is followed by counterstaining with an aqueous or alcoholic solution of eosin Y, which colours eosinophilic other structures in various shades of red, pink and orange. The staining of nuclei by hemalum does not require the presence of DNA and is probably due to binding of the dye-metal complex to arginine-rich basic nucleoproteins such as histones. Eosin is a fluorescent red dye resulting from the action of bromine on fluorescein. It can be used to stain cytoplasm for examination under the microscope. Structures that stain readily with eosin are termed eosinophilic. Eosin is most often used as a counterstain to haematoxylin in H&E (haematoxylin and eosin) staining. Eosin stains red blood cells intensely red. Eosin is an acidic dye and shows up in the basic parts of the cell, i.e. the cytoplasm.

Liver specimens stained with H&E will, therefore, typically display blue nuclei, with the cytoplasm and extracellular matrix in different shades of pink. We used a 40× light microscope, following H & E staining, to take pictures and compared the dosed versus non-dosed groups accordingly. In this protocol, tissues are taken from animal experiments, preserved in paraffin, sliced (approximately 4-9 μm sections) on a microtome, and placed on slides, ready for staining and/or IHC analysis.

Solutions/Buffers

>98% Xylene (Fisher Extra Pure SLR Fisher Chemical X/0200/17)

>98% Propanol (Sigma Aldrich, cat no. 19516)

H2O (distilled)

Hemotoxylin solution (Sigma Aldrich, cat no. MHS1)

Eosin Y solution (Sigma Aldrich, cat no. E4009)

For this experiment, mice (OTC hemizygous males) were dosed over an 8 day period with recombinant human GS protein intraperitoneally at 40 mg/kg (described previously), and—following cull—livers were harvested. The mouse livers were divided in to two groups for the purposes of this study: 1. Recombinant human GS (AM-535), 2. control/vehicle. Mouse livers in both groups were examined for basic pathology, including H & E staining.

In all 6 enzyme-related Urea Cycle Disorders, a steatotis/fatty liver-like disease has been noted [Bigot et al. 2017 'Liver involvement in urea cycle disorders: a review of the literature]. The Urea Cycle has been shown to be dysregulated in NAFLD (non-alcoholic fatty liver disease) [Chiara et al 2018 'Urea cycle dysregulation in non-alcoholic fatty liver disease].

Paraffin tissue blocks (fixed and paraffinised) were kept cool on a Lamb cooling block (Model TC-10), at −10 C. Samples were sliced with a microtome. Liver slices were sliced at 4 μm thickness; kidney at 4 μm; brain tissue at 8 μm. Following slicing, tissues were placed in a heated water bath (heated to 55 degrees Celsius) for a few seconds, and then placed on a slide (tissue is placed on to the slide via dipping in to the water with the slide).

1. Deparaffinize tissue: 'dunk' tissue for 45 sec in xylene
2. Remove xylene and fixate: ' dunk' for 45 sec in propanol
3. Hematoxylin stain: apply 1 drop of Hematoxylin stain per 50-100 mm2 and wait 45 sec. (approximately 5 drops per slide is usually required)
4. Hematoxylin rinsing: rinse hematoxylin residues vigorously with warm (30° C.) water (distilled $H_2O$ recommended) for approximately 45 sec
5. Eosin stain: apply 2-3 drops of Eosin stain and wait 30 sec
6. Eosin rinsing: rinse again with cold water (distilled $H_2O$) for 15 sec
7. Final wash: dip 45 sec in propanol and then 45 sec in xylene Results Nuclei should be blue, cytoplasm pink to red.

Recombinant human GS treated mice showed (see FIG. 6) show normal liver architecture and cellular integrity, with very little fibrosis and overall reasonably healthy livers. In contrast, mice in the control (non-dosed) group showed significantly less healthy livers, indicative of steatosis and fatty-liver like disease.

Hepatocellular steatosis can be identified by either the presence of single large fat droplets, alongside nuclei dislocation to the cell's periphery (macrovesicular steatosis), or small lipid droplets and no nuclei displacement (microvesicular steatosis). The former is typical of NAFLD and the latter associates with inflammation in NASH. These results demonstrate that both NAFLD and NASH may be involved in this OTC mouse model, and that a definite—and very marked—improvement in the health of the livers of the dosed animals can be seen (see FIG. 6).

These results indicate that GS therapy is a potential tool for treatment and reversal of hepatic steatosis, including fatty liver, NASH (non-alcoholic steatohepatitis) and associated liver disease disorders. In short term dosing (8 days), the fibrotic-like phenotype of AM-535-dosed (recombinant GS enzyme) (OTC hemizygous) mice was significantly different to the control mice, indicating that in this short period that a reversal and inhibition of fatty-liver-type progression was occurring. This is the first—very strong—indication that GS therapy could be useful in the treatment and reversal of steatosis and associated diseases (including NAFLD, NASH and fibrosis).

Example 6 Mouse MCD Study

The most widely used diet to induce NAFLD/NASH is the methionine-choline deficient (MCD) diet. Standard MCD diet also has a high content of sucrose (40% of energy) and is moderately enriched with fat (10-20%). It is a very reproducible model [5].

Figure 7:
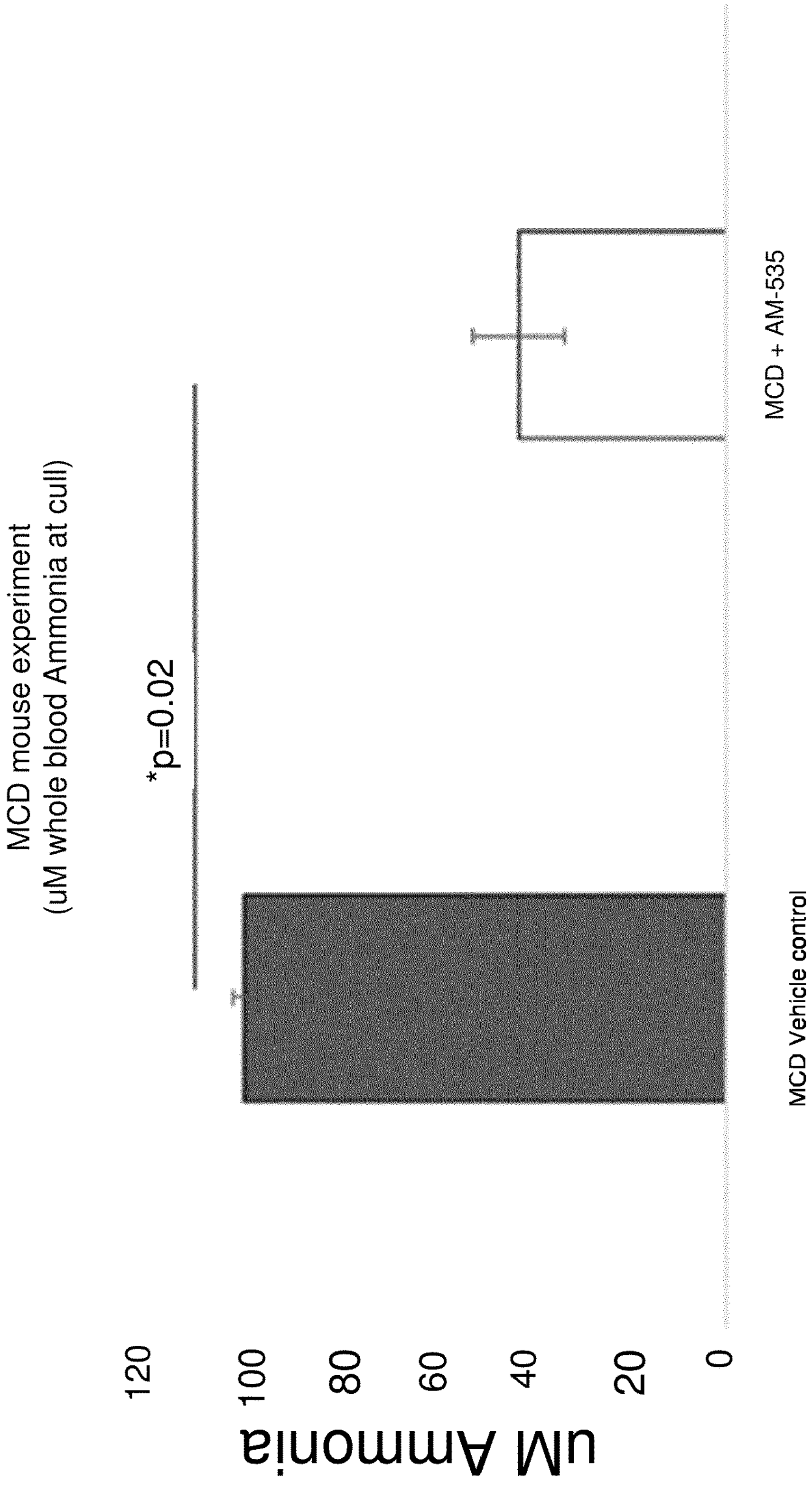
FIG. 7 shows the ammonia levels in the control and GS dosed mice as described in Example 6.

Pegylated human recombinant GS, with N terminal GGGS-HHHHHH-GGGGS linker/tag sequences was used.) A study was carried out to investigate whether this GS (referred to in FIG. 7 as AM535) is effective in this model, and could potentially reduce fat and be a potential candidate for NAFLD/NASH indications.

Methods

Mouse model background, phenotype:

Mice: C57/Black

Gender: Female

Weight: 25 g-30 g

Age: >7 weeks

MCD Diet Dosage:

5 g per day/per mice+drug interventions where appropriate

MCD Diet Make-Up:

Methionine/Choline Deficient Diet Composition (Amount g/kg diet):

Sucrose 455.3 gm

Corn Starch 200.0 gm

Corn Oil 100.0 gm

Alphacel Non-Nutritive Bulk 30.0 gm

AIN 76 Mineral Mix 35.0 gm

AIN 76 Mineral Mix composition (gm/kg):

Calcium Phosphate Dibasic 500.00 gm

Sodium Chloride 74.00 gm

Potassium Citrate Monohydrate 220.00 gm

Potassium Sulfate 52.00 gm

Magnesium Oxide 24.00 gm

Manganese Carbonate (43-48% Mn) 3.50 gm

Ferric Citrate (16-17% Fe) 6.00 gm

Zinc Carbonate (70% ZnO) 1.60 gm

Cupric Carbonate (53-55% Cu) 0.30 gm

Potassium Iodate 0.01 gm

Sodium Selenite 0.01 gm

Chromium Potassium Sulfate 0.55 gm

Sucrose, finely powdered 118.00 gm-Dicalcium Phosphate 3.0 gm, L-Alanine 3.5 gm, L-Arginine Hydrochloride 12.1 gm, L-Asparagine Monohydrate 6.0 gm, L-Aspartic Acid 3.5 gm, L-Cystine 3.5 gm, L-Glutamic Acid 40.0 gm, Glycine 23.3 gm, L-Histidine Hydrochloride 4.5 gm, L-Isoleucine 8.2 gm, L-Leucine 11.1 gm, L-Lysine Hydrochloride 18.0 gm, L-Phenylalanine 7.5 gm, L-Proline 3.5 gm, L-Serine 3.5 gm, L-Threonine 8.2 gm, L-Tryptophan 1.8 gm, L-Tyrosine 5.0 gm, L-Valine 8.2 gm, DL-alpha-Tocopherol Acetate (250 u/gm) 0.484 gm, Vitamin A Palmitate (250,000 u/gm) 0.0792 gm, Vitamin D3 (400,000 u/gm) 0.0055 gm, Ethoxyquin 0.02 gm, Vitamin Mix—Biotin 0.0004 gm, D-Calcium Pantothenate 0.0661 gm, Folic Acid 0.002 gm, Inositol 0.1101 gm, Menadione 0.0496 gm, Niacin 0.0991 gm, p-Aminobenzoic Acid 0.1101 gm, Pyridoxine Hydrochloride 0.0220 gm, Riboflavin 0.022 gm, Thiamine Hydrochloride 0.022 gm, Vitamin B12 (0.1% trit.) 0.0297 gm, Ascorbic acid 1.0166 gm, Corn Starch 3.4503 gm Method/Outline of Study:

MCD mice were made comfortable and housed in the animal facility for at least one week before diet was initiated. The study ran for 2.5-4 weeks, pending individual requirements.

Therapeutic interventions were performed according to instructions. Blood ammonia was taken at cull point, along with tissues and histology performed. This MCD study was performed for 18 days, with 2 doses per week of GS as defined above given i.p. at 25 mg/kg. In total, the mice received 6 doses of GS as defined above. Organs and blood were harvested for analysis.

Study Groups:

−2× vehicle control (saline injected)

−3× GS dosed.

Post-Cull Analysis:

Ammonia was measured by the Ammonia Fuji checker, using 10 ul of mouse blood (fresh)—according to manufacturers instructions. In brief, 10 ul is applied to the cartridge, inserted in to the Fuji machine. The machine (which contains bromophenol blue) heats the whole blood sample. When the sample is heated, NH3 gas is released from whole blood, and mixes with the bromophenol blue. The sample is then read by the Fuji checker at OD 600 nM to give an estimation of ammonia (in micromolar/uM), which is given to the operator on the console 2 mins post insertion of the cartridge.

Details on the Ammonia Fuji checker and cartridges used are publicly available through Fuji Film's website and related Product pages (reference NH3-W_9903230).

Livers were analysed via H&E staining as described in Example 5, and a fat count was performed digitally (mFPA), according to methods outlined in [6, 7].

Results

Ammonia Levels Vs Control Mice

Ammonia levels were measured immediately post-cull and 10 microlitres of whole blood was taken from each mouse and analysis was performed on the Fuji ammonia checker. Ammonia was significantly raised in the MCD vehicle control mice (at approximately 100 □□, considered pathogenic), with GS dosed animals showing a very highly reduced ammonia level (see FIG. 7), down to very low baseline (non pathogenic) levels of ammonia (approximately 40 □□average). This reduction was shown to be highly significant.

H&E Staining and Fat Count:

H&E staining was performed according to protocol described above in Example 5. Liver slices were subsequently analysed digitally to count fat in dosed vs control groups.

Figure 8:
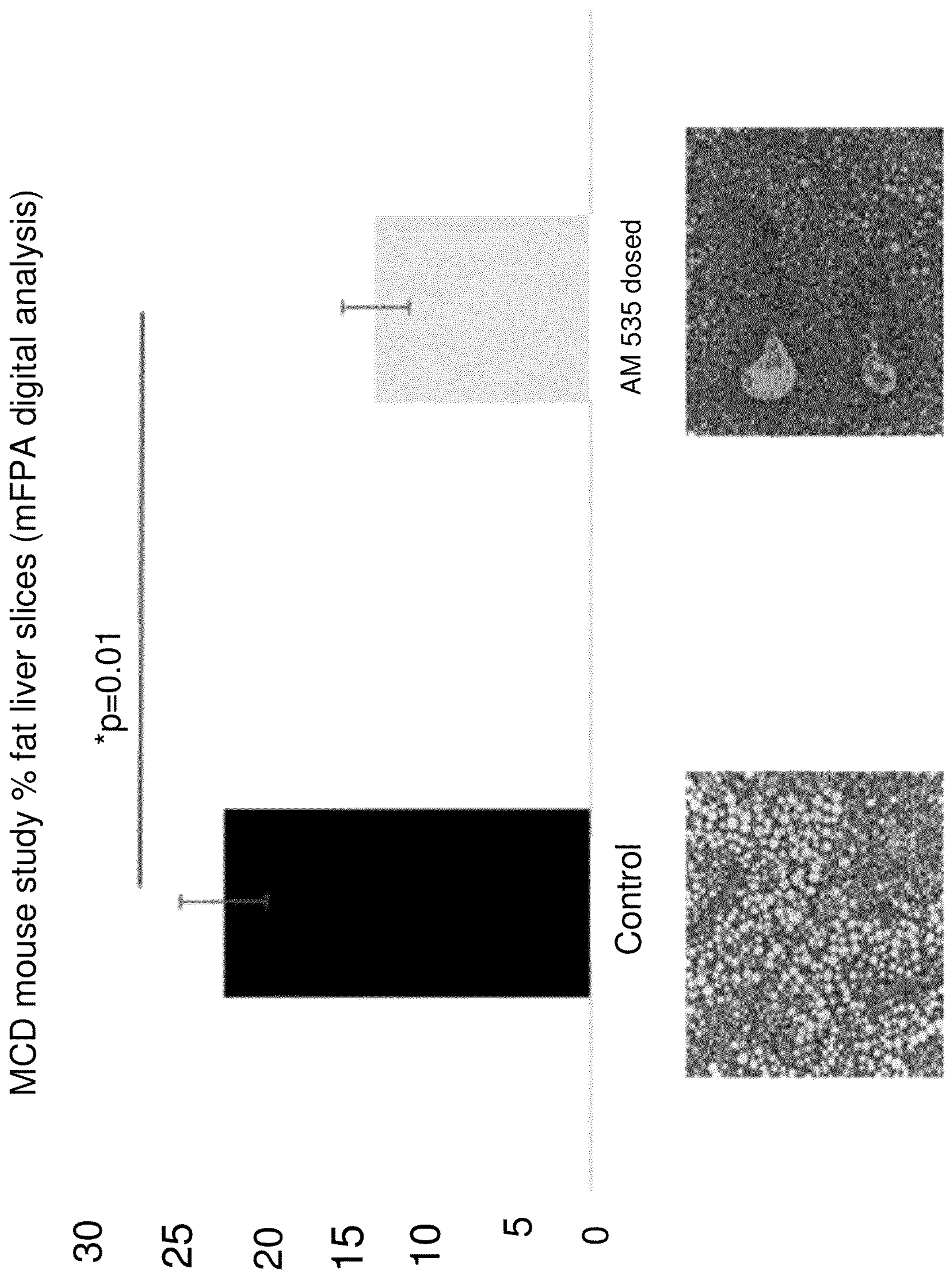
FIG. 8 shows the percentage (%) fat in liver slices in control, according to digital FPA analysis in GS (AM 535) dosed MCD mice as described in Example 6.

It could be seen from an independent mFPA fat count (See FIG. 8) that dosed animals were significantly lower in fat, when compared to the vehicle control animals. Therefore, it could be concluded that GS significantly reduces fat in the liver in this MCD model.

Summary

It was found that GS reduced levels of ammonia very significantly—from pathogenic levels (approx. 100 □M) to low, non-pathogenic levels of ammonia (approx. 40 □M). This is the third model in which GS has demonstrated very significantly reduced levels of ammonia. Therefore, GS is likely an excellent candidate to further pursue in the hyperammonemia-associated conditions (including Urea Cycle disorders, Hepatic Encephalopathy and Organic acidemias).

From H&E staining, and a subsequent fat count, we also showed that recombinant GS significantly reduced levels of fat. Both the MCD and OTC mouse model have shown reduced levels of fat compared to vehicle controls.

Example 7

High Fat High Cholesterol Rat

Principle/Background

The High Fat High Cholesterol (HFHC) rat is a model of progressive NAFLD (non-alcoholic fatty liver disease), steatohepatitis, fibrosis and eventual cirrhosis [9-11].

Objective

To determine if AM-535, dosed i.p. twice weekly for the final 7 weeks of a 16 week model (at approximately 10 mg/kg) can alter the course of this model and improve the disease progression and outcome.

Outline/Method of Study 8 week old Male Sprague Dawley rats were obtained from Charles River, UK. They were housed and made comfortable for at least a week prior to the study. Male SD rats 220-250 g were fed a high fat high cholesterol (100 g) or chow (100 g) diet for 16 weeks and randomised to receive intraperitoneal GS (pegylated human recombinant GS, with N terminal GGGS-HHHHHH-GGGGS linker/tag sequences, also referred to as AM-535) or vehicle twice per week from week 9-16 inclusive. Following cull, blood was obtained via cardiac puncture, and organs were harvested for analysis and pathology.

Groups:

Normal chow diet (+vehicle) n=4

HFHC diet (+vehicle [saline]) n=4

HFHC diet (+GS) n=4

Total animals for treatment study n=12

High Fat High Cholesterol Diet Composition

| | D09052204Y (Charles River, UK) | |
|---|---|---|
| Product # | gm % | kcal % |
| Protein | 27 | 20 |
| Carbohydrate | 19 | 15 |
| Fat | 39 | 65 |
| Total | | 100 |
| kcal/gm | 5.3 | |
| Ingredient | gm | kcal |
| Casein, 30 Mesh | 200 | 800 |
| L-Cystine | 3 | 12 |
| Corn Starch | 0 | 0 |
| Maltodextrin 10 | 97.5 | 390 |
| Sucrose | 40 | 160 |
| Cellulose, BW200 | 50 | 0 |
| Soybean Oil | 25 | 225 |
| Cocoa Butter | 270 | 2430 |
| Lard | 0 | 0 |
| Mineral Mix, S10026 | 10 | 0 |
| DiCalcium Phosphate | 13 | 0 |
| Calcium Carbonate | 5.5 | 0 |
| Potassium Citrate, 1 H2O | 16.5 | 0 |
| Vitamin Mix, V10001 | 10 | 40 |
| Choline Bitartrate | 2 | 0 |
| Cholesterol | 15.3 | 0 |
| Sodium Cholate | 3.8 | 0 |

Liver tissue was preserved in paraffin, sliced (approximately 8 μm sections) on a microtome, and placed on slides, ready for staining. Sirius Red staining was performed to detect collagen: this technique is based on the tight-binding of the stain sulfonic acid groups with the basic groups of collagen fibers.

In brief, the staining protocol as follows:

1. Paraffin sections of liver were de-waxed and hydrated; 2 Stained in picro-sirius red solution ((Direct 80', cat no. 2610-10-8) for one hour; 3. Sections were vigorously shaken or blotted very gently with damp filter paper; 4. Sections were dehydrated in three changes of 100% ethanol; 5. Finally, sections were cleared in xylene, mounted with DPX mounting medium and imaged.

Results

TABLE 1

Blood ammonia and weights. Note, ammonia is not elevated in any group. The liver:body weight ratio average was also somewhat lower in the treated vs vehicle group (0.047 vs 0.051), though this was not statistically significant.

| XR | Group | Treatment | Ammonia (μmol/L) | Liver Weight (g) | Final Body weight (g) | Liver:Body weight |
|---|---|---|---|---|---|---|
| 3941 | Naïve | Nil | 30 | 16.5 | 590 | 0.028 |
| 3942 | Naïve | Nil | 54 | 20.5 | 616 | 0.033 |
| 3943 | Naïve | Nil | 38 | 13.5 | 487 | 0.028 |
| 3944 | Naïve | Nil | 27 | 16.5 | 556 | 0.030 |
| 3945 | HFHC | Vehicle | 32 | 35 | 586 | 0.060 |
| 3946 | HFHC | Vehicle | 51 | 25.5 | 560 | 0.046 |
| 3947 | HFHC | Vehicle | 42 | 29.5 | 578 | 0.051 |
| 3948 | HFHC | Vehicle | 46 | 26.5 | 560 | 0.047 |
| 3949 | HFHC | AM-535 | 35 | 33 | 620 | 0.053 |
| 3950 | HFHC | AM-535 | 51 | 25.5 | 545 | 0.047 |
| 3951 | HFHC | AM-535 | 37 | 24.5 | 510 | 0.048 |
| 3952 | HFHC | AM-535 | 44 | 23.5 | 567 | 0.041 |

Blood ammonia results showed that no single group was elevated in terms of ammonia (including vehicle HFHC rats), and a slightly reduced liver:body weight ratio was noted in the GS (AM-535) treated HFHC rats when compared to vehicle.

Liver Pathology Collagen Proportionate Area (CPA) Results

Figure 9:
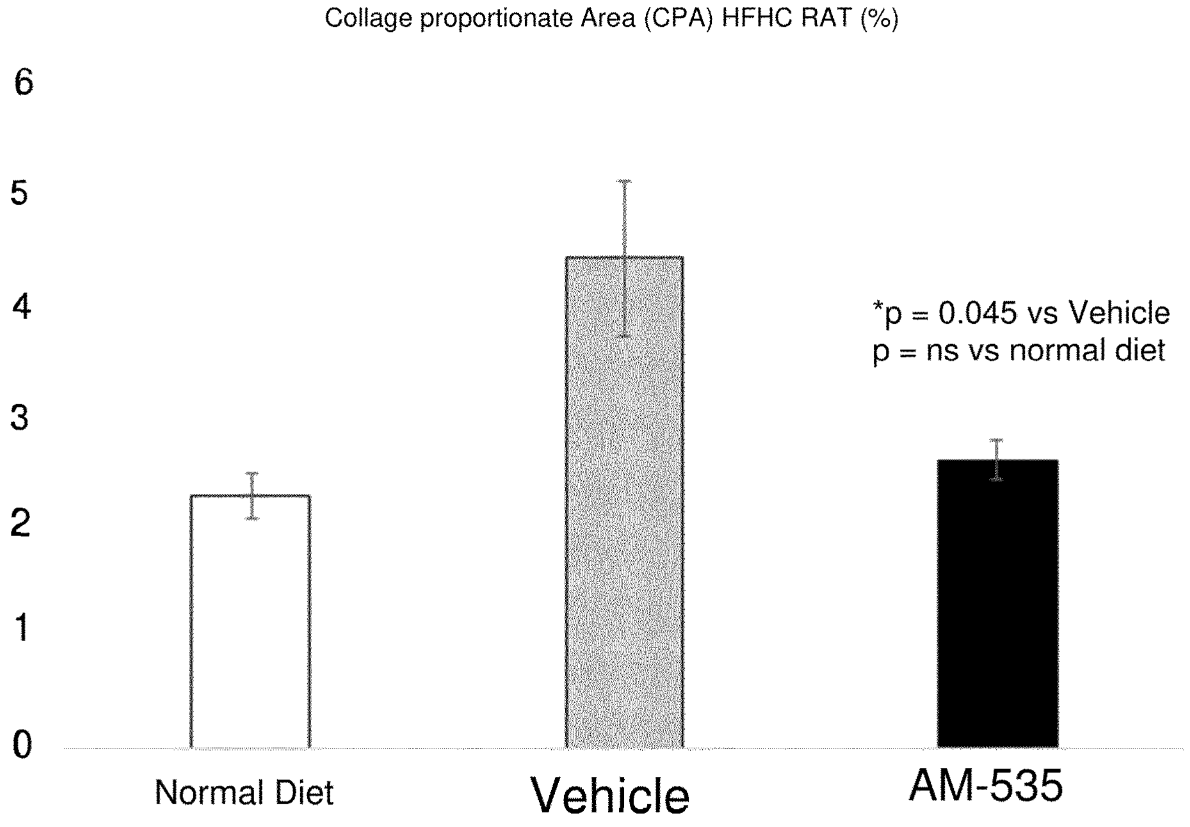
FIG. 9 shows the results of HFHC rat CPA (collagen proportionate area) in graphical form, according to example 7.
Figure 10:
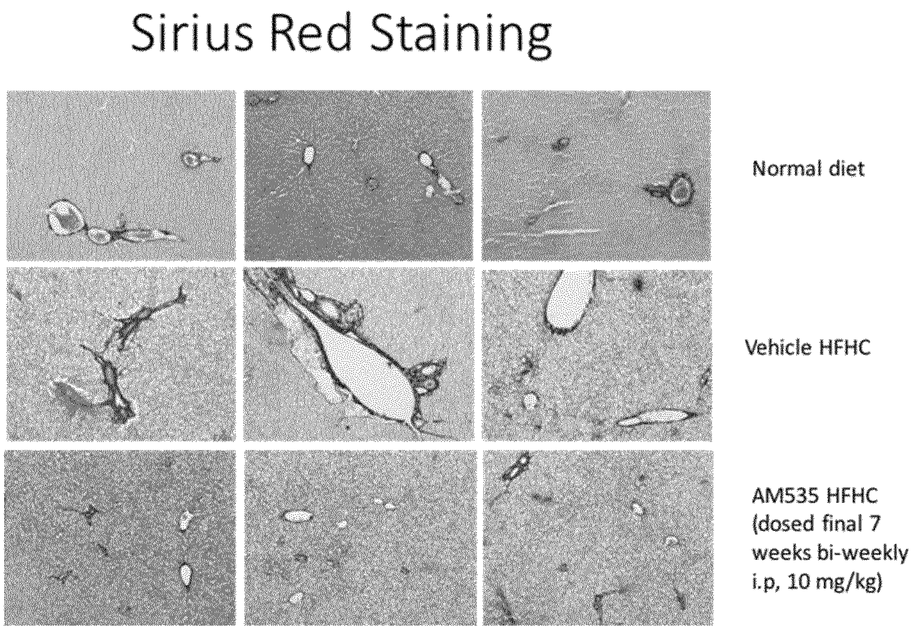
FIG. 10 shows the impact of GS enzyme (AM-535) after 7 weeks of dosing bi-weekly on fibrosis with Sirius red stain; demonstrating the same CPA levels as the normal, non-HFHC diet animals, according to example 7.

FIG. 9 shows GS after 7 weeks of dosing bi-weekly had a significant reduction in the CPA (Collagen proportionate area), and was able to demonstrate the same CPA levels as the normal diet animals.

Analysis showed CPA (collagen proportionate area) was significantly lowered in the HFHC AM-535 dosed animals (Sirius Red stained liver slices). Collagen proportionate area (CPA) measurement quantifies fibrous tissue in liver biopsies or slices (of human patients or animals) by measuring the amount of collagen deposition as a proportion of the total biopsy area [11,12]. CPA predicts clinical outcomes in patients with fatty liver and cirrhosis [13,14].

Fibrosis is the formation of an abnormally large amount of scar tissue in the liver. It occurs when the liver attempts to repair and replace damaged cells. Therefore, it is a marker of late-stage fatty liver disease and cirrhosis.

Summary

In this particular study, HFHC rats were fed on a high fat, high cholesterol diet for 16 weeks (or normal diet for naive control animals). In the final 7 weeks, the HFHC diet rats were dosed either with vehicle (saline) or GS twice weekly at approximately 10 mg/kg. After cull, clinical blood parameters were measured. Similar levels were observed when comparing the GS HFHC rats to vehicle HFHC control on most blood and weight parameters.

GS was able to bring down CPA to normal diet levels in a rat subjected to a HFHC diet very significantly, in contrast to the vehicle HFHC animals, in which the CPA was measured at quite high levels. As ammonia was not elevated in any group, the HFHC model is not a hyperammonemia model. In addition, it is feasible that dosing may be increased from 10 mg/kg twice weekly especially given the very low toxicity and high safety profile of this enzyme therapy. GS dosing was started at 7 weeks, and in view of the fact that at 9 weeks, rats would already have advanced liver disease, these data are particularly interesting and shows that GS is a potential treatment for liver fibrosis.

REFERENCES

[1] Riggs A. The amino acid composition of some mammalian hemoglobins: mouse, guinea pig, and elephant. J Biol Chem 1963; 238:2983-2987.

[2] Balata S, Olde Damink S W, Ferguson K, Marshall I, Hayes P C, Deutz N E, Williams R, Wardlaw J, Jalan R. Induced hyperammonemia alters neuropsychology, brain MR spectroscopy and magnetization transfer in cirrhosis. Hepatology 2003; 37:931-939.

[3] Stewart-Wallace A M. A biochemical study of cerbral tissue, and of changes in cerebral oedema. Brain 1939; 62: 426-38.

[4] Traber P G, Ganger D R, Blei A T. Brain edema in rabbits with galactosamine-induced fulminant hepatitis. Regional differences and effects on intracranial pressure. Gastroenterology 1986; 91: 1347-56.

Kiernan J A (2008) Histological and Histochemical Methods: Theory and Practice. 4th ed. Bloxham, UK: Scion.

Lillie R D, Pizzolato P, Donaldson P T (1976) Nuclear stains with soluble metachrome mordant lake dyes. The effect of chemical endgroup blocking reactions and the artificial introduction of acid groups into tissues. Histochemistry 49: 23-35.

Llewellyn B D (2009) Nuclear staining with alum-hematoxylin. Biotech. Histochem. 84: 159-177.

[5] Machado et al; *PLoS One.* 2015; 10(5): e0127991

[6, 7] Hall et al, Liver Int. 2014, October 34(9) 1417-1427 and Hall et al, Liver Int. 2013 July 33(6) 926-935

[8] Marques et al Adipocyte 2016 5(1) 11-21

[9] Ichimura et al Hepatology Research Vol 45 Issue 4 2015 458-469

[10] Jensen et al Diabetology and Metabolic Syndrome 10 4(2018)

[11] Buzetti et al Alimentary Pharmacology and Therapeutics Vol 49 Issue 9 1214-1222

[12] Hall et al, Histopathology 2013 62(3) 421-430

[13] Xie et al Heptobiliary Pancreat Dis Int 2011 10(5) 497-501

[14] Huang et al Liver Int 2013 September 33(8) 1249-1256

BRIEF DESCRIPTION OF THE SEQUENCE LISTINGS:

SEQ ID NO. 1 [Full human protein]

MTTSASSHLNKGIKQVYMSLPQGEKVQAMYIWIDGTGEGLRCKTRTLDSEPKC

VEELPEWNFDGSSTLQSEGSNSDMYLVPAAMFRDPFRKDPNKLVLCEVFKYNR

RPAETNLRHTCKRIMDMVSNQHPWFGMEQEYTLMGTDGEEPFGWPSNGFPGPQ

GPYYCGVGADRAYGRDIVEAHYRACLYAGVKIAGTNAEVMPAQWEFQIGPCE

GISMGDHLWVARFILHRVCEDFGVIATFDPKPIPGNWNGAGCHTNFSTKAMRE

ENGLKYIEEAIEKLSKRHQYHIRAYDPKGGLDNARRLTGFRETSNINDFSAGVA

NRSASIRIPRTVGQEKKGYFEDRRPSANCDPFSVTEALIRTCLLNETGDEPFQYK

N

SEQ ID. NO. 2

(ONLY Methionine is cleaved for the mature protein in vivo):

TTSASSHLNKGIKQVYMSLPQGEKVQAMYIWIDGTGEGLRCKTRTLDSEPKCV

EELPEWNFDGSSTLQSEGSNSDMYLVPAAMFRDPFRKDPNKLVLCEVFKYNRR

PAETNLRHTCKRIMDMVSNQHPWFGMEQEYTLMGTDGHPFGWPSNGFPGPQG

PYYCGVGADRAYGRDIVEAHYRACLYAGVKIAGTNAEVMPAQWEFQIGPCEG

ISMGDHLWVARFILHRVCEDFGVIATFDPKPIPGNWNGAGCHTNFSTKAMREE

NGLKYIEEAIEKLSKRHQYHIRAYDPKGGLDNARRLTGFHETSNINDFSAGVAN

RSASIRIPRTVGQEKKGYFEDRRPSANCDPFSVTEALIRTCLLNETGDEPFQYKN

SEQ ID NO. 3 cDNA

CGAGAGTGGGAGAAGAGCGGAGCGTGTGAGCAGTACTGCGGCCTCCTCTCCTCTCCTAAC

CTGCTCTCGCGGCCTACCTTTACCCGCCCGCCTGCTCGGCGACCAGAACACCTTCCACCA

TGACCACCTCAGCAAGTTCCCACTTAAATAAAGGCATCAAGCAGGTGTACATGTCCCTGC

CTCAGGGTGAGAAAGTCCAGGCCATGTATATCTGGATCGATGGTACTGGAGAAGGACTGC

GCTGCAAGACCCGGACCCTGGACAGTGAGCCCAAGTGTGTGGAAGAGTTGCCTGAGTGGA

ATTTCGATGGCTCCAGTACTTTACAGTCTGAGGGTTCCAACAGTGACATGTATCTCGTGC

CTGCTGCCATGTTTCGGGACCCCTTCCGTAAGGACCCTAACAAGCTGGTGTTATGTGAAG

TTTTCAAGTACAATCGAAGGCCTGCAGAGACCAATTTGAGGCACACCTGTAAACGGATAA

TGGACATGGTGAGCAACCAGCACCCCTGGTTTGGCATGGAGCAGGAGTATACCCTCATGG

GGACAGATGGGCACCCCTTTGGTTGGCCTTCCAACGGCTTCCCAGGGCCCCAGGGTCCAT

-continued

ATTACTGTGGTGTGGGAGCAGACAGAGCCTATGGCAGGGACATCGTGGAGGCCCATTACC

GGGCCTGCTTGTATGCTGGAGTCAAGATTGCGGGGACTAATGCCGAGGTCATGCCTGCCC

AGTGGGAATTTCAGATTGGACCTTGTGAAGGAATCAGCATGGGAGATCATCTCTGGGTGG

CCCGTTTCATCTTGCATCGTGTGTGTGAAGACTTTGGAGTGATAGCAACCTTTGATCCTA

AGCCCATTCCTGGGAACTGGAATGGTGCAGGCTGCCATACCAACTTCAGCACCAAGGCCA

TGCGGGAGGAGAATGGTCTGAAGTACATCGAGGAGGCCATTGAGAAACTAAGCAAGCGGC

ACCAGTACCACATCCGTGCCTATGATCCCAAGGGAGGCCTGGACAATGCCCGACGTCTAA

CTGGATTCCATGAAACCTCCAACATCAACGACTTTTCTGGTGGTGTAGCCAATCGTAGCG

CCAGCATACGCATTCCCCGGACTGTTGGCCAGGAGAAGAAGGGTTACTTTGAAGATCGTC

GCCCCTCTGCCAACTGCGACCCCTTTTCGGTGACAGAAGCCCTCATCCGCACGTGTCTTC

TCAATGAAACCGGCGATGAGCCCTTCCAGTACAAAAATTAAGTGGACTAGACCTCCAGCT

GTTGAGCCCCTCCTAGTTCTTCATCCCACTCCAACTCTTCCCCCTCTCCCAGTTGTCCCG

ATTGTAACTCAAAGGGTGGAATATCAAGGTCGTTTTTTTTCATTCC

SEQ ID NO. 4: GS protein grown in bacteria, used in Example 1
MGSSHHHHHHGGGGSMTTSASSHLNKGIKQVYMSLPQGEKVQAMYIWIDGTG

EGLRCKTRTLDSEPKCVEELPEWNFDGSSTLQSEGSNSDMYLVPAAMFRDPFR

KDPNKLVLCEVFKYNRRPAETNLRHTCKRIMDMVSNQHPWFGMEQEYTLMGT

DGHPFGWPSNGFPGPQGPYYCGVGADRAYGRDIVEAHYRACLYAGVKIAGTN

AEVMPAQWEFQIGPCEGISMGDHLWVARFILHRVCEDFGVIATFDPKPIPGNWN

GAGCHTNFSTKAMREENGLKYIEEAIEKLSKRHQYHIRAYDPKGGLDNARRLT

GFHETSNINDFSAGVANRSASIRIPRTVGQEKKGYFEDRRPSANCDPFSVTEALI

RTCLLNETGDEPFQYKN

SEQ ID NO. 5 cDNA (bacterial optimised cDNA used in Example 1).
ATGGGCAGCAGCCACCACCATCACCACCACGGCGGCGGCGGTAGCATGACC

ACCTCGGCAAGCAGCCACCTGAATAAAGGCATCAAACAGGTGTATATGTCT

CTGCCGCAGGGTGAAAAAGTTCAAGCCATGTACATTTGGATCGATGGCACC

GGTGAAGGCCTGCGTTGCAAAACCCGCACGCTGGACTCAGAACCGAAATGT

GTGGAAGAACTGCCGGAATGGAACTTTGATGGTAGCTCTACGCTGCAGTCG

GAAGGCAGTAATTCCGACATGTATCTGGTTCCGGCGGCCATGTTTCGTGATC

CGTTCCGCAAAGACCCGAACAAACTGGTGCTGTGCGAAGTTTTTAAATACA

ACCGTCGCCCGGCGGAAACCAATCTGCGTCATACGTGTAAACGCATTATGG

ATATGGTCAGCAACCAGCACCCGTGGTTCGGTATGGAACAAGAATATACCC

TGATGGGTACGGATGGCCATCCGTTTGGTTGGCCGAGCAATGGTTTCCCGGG

TCCGCAGGGTCCGTATTACTGCGGTGTCGGCGCAGATCGTGCTTACGGTCGC

GACATTGTGGAAGCACACTATCGTGCTTGTCTGTACGCGGGTGTTAAAATCG

CCGGCACCAATGCAGAAGTCATGCCGGCTCAGTGGGAATTTCAAATTGGCC

CGTGCGAAGGTATCAGCATGGGCGATCATCTGTGGGTTGCTCGTTTCATCCT

GCACCGCGTCTGTGAAGATTTTGGTGTGATTGCGACCTTCGACCCGAAACCG

ATCCCGGGCAACTGGAATGGTGCTGGCTGCCATACCAACTTTAGCACGAAA

GCGATGCGTGAAGAAAATGGCCTGAAATACATCGAAGAAGCAATCGAAAA

ACTGTCTAAACGTCATCAGTATCACATTCGCGCCTACGATCCGAAAGGCGGT

CTGGACAACGCACGTCGCCTGACCGGTTTTCACGAAACGAGCAACATCAAT

-continued

GATTTCTCTGCGGGCGTTGCCAATCGCTCAGCCTCGATTCGTATCCCGCGCA

CCGTCGGTCAAGAGAAAAAAGGCTATTTTGAAGATCGTCGCCCGAGTGCAA

ACTGTGACCCGTTCTCCGTGACGGAAGCCCTGATCCGCACCTGTCTGCTGAA

TGAAACCGGCGATGAACCGTTCCAATACAAAAAT

SEQ ID NO. 6 [*Lactobacillus acidophilus* strain 30SC GS]
>tr|F0TG87|F0TG87_LACA3 Glutamine synthetase
OS = *Lactobacillus acidophilus* (strain 30SC)

MSKQYTTEEIRKEVADKDVRFLRLCFTDINGTEKAVEVPTSQLDKVLTNDIRFD

GSSIDGFVRLEESDMVLYPDFSTWSVLPWGDEHGGKIGRLICSVHMTDGKPFA

GDPRNNLKRVLGEMKEAGFDTFDIGFEMEFHLFKLDENGNWTTEVPDHASYFD

MTSDDEGARCRREIVETLEEIGFEVEAARKEVGDGQQHDFRFDDALTTADRCQ

TFKMVARHIARKHGLFATFMAKPVEGQAGNGMHNNMSLFKNKHNVFYDKDG

EFHLSNTALYFLNGILEHARAITAIGNPTVNSYKRUPGFEAPVYIAWAAKNRSP

LVRIPSAGEINTRLEMRSADPTANPYLLLAACLTAGLKGIKEQKMPMKPVEENI

FEMTEEERAEHGIKPLPTTLHNAIKAFKEDDLIKSALGEHLTHSFIESKELEWSK

YSQSVSDWERQRYMNW

SEQ ID NO. 7 [*Zea Mays* GS] (corn/Maize GS)
>tr|B4G1P1|B4G1P1_MAIZE Glutamine synthetase

MACLTDLVNLNLSDNTEKIIAEYIWIGGSGMDLRSKARTLSGPVTDPSKLPKWN

YDGSSTGQAPGEDSEVILYPQAIFKDPFRRGNNILVMCDCYTPAGEPIPTNKRYN

AAKIFSSPEVAAEEPWYGIEQEYTLLQKDTNWPLGWPIGGFPGPQGPYYCGIGA

EKSFGRDIVDAHYKACLYAGINISGINGEVMPGQWEFQVGPSVGISSGDQVWV

ARYILERITEIAGVVVTFDPKPIPGDWNGAGAHTNYSTESMRKEGGYEVIKAAIE

KLKLRHREHIAAYGEGNERRLTGRHETADINTFSWGVANRGASVRVGRETEQN

GKGYFEDRRPASNMDPYVVTSMIAETTIIWKP

In addition to the foregoing, the same Sequence Listings are provided in computer readable form encoded in a file submitted herewith and herein incorporated by reference. The information recorded in computer readable form is identical to the written Sequence Listings provided herein, pursuant to 37 C.F.R. § 1.821(f).

The invention claimed is:

1. A method of reducing or eliminating fat deposits or fibrosis in a liver of a subject with fatty liver disease or an associated liver disease comprising hepatitis, fibrosis, cirrhosis, or liver cancer, wherein the subject has fat deposits in, or fibrosis of, the liver, said method comprising:

administering a glutamine synthetase (GS) protein to said subject; or administering an expression vector encoding GS to said subject.

2. The method according to claim 1, wherein the administering step reduces or eliminates fat deposits and/or fibrosis in the liver in the subject.

3. The method according to claim 1, wherein the method further comprises administering an ammonia lowering agent to the subject.

4. The method according to claim 1, comprising simultaneous, sequential or subsequent administration of GS and an ammonia lowering agent to said subject.

5. The method according to 1, wherein the subject is previously diagnosed as having fatty liver disease.

6. The method according to claim 1, wherein GS is:

a protein and comprises an amino acid sequence that is at least 50% identical to the amino acid sequence set forth in SEQ ID NO. 1, or is an enzymatically-active fragment thereof; or a nucleic acid molecule encoding a GS protein or a biologically active fragment or variant thereof and provided in an expression vector.

7. The method according to claim 1, wherein fatty liver disease is an acquired fatty liver disease, or a genetically derived fatty liver disease.

8. The method according to claim 3, wherein the ammonia lowering agent is selected from the group consisting of a nitrogen scavenger, an ion exchange resin, an ammonia, an engineered microbiome that removes ammonia, and gut ammonia detoxification or removal methods.

9. The method according to claim 1, wherein the GS protein is linked to a moiety comprising a protein, a peptide, a non-protein polymer, or an affinity tag.

10. The method according to claim 1, wherein the GS protein comprises an N terminal peptide linker.

11. The method according to claim 1, wherein the GS protein or the expression vector is in a form suitable for subcutaneous or intravenous administration.

12. The method according to claim 1, wherein the GS protein is in a monomeric or multimeric form.

13. The method according to claim 4, wherein the ammonia lowering agent is a nitrogen scavenger selected from the group consisting of a pharmaceutically acceptable salt of phenylacetic acid or a pharmaceutically acceptable pro-drug thereof, a pharmaceutically acceptable salt of phenylbutyric acid or a pharmaceutically acceptable pro-drug thereof, glycerol phenylbutyrate or a pharmaceutically acceptable pro-drug thereof, a pharmaceutically acceptable salt of benzoic acid or a pharmaceutically acceptable pro-drug thereof, and an ammonia binding resin.

14. The method according to claim 9, wherein the non-protein polymer moiety is a polyethylene glycol (PEG), and the PEG is an N terminal aldehyde PEG.

15. The method according to claim 9, wherein the GS protein is linked to the moiety via a linker, and the linker comprises a His-tag and a 2-10 mer peptide sequence.

16. The method according to claim 9, wherein the GS protein is linked to the moiety via a linker, and the linker comprises a His-tag and the sequence GGGGS.

17. The method according to claim 13, wherein the ammonia lowering agent is sodium phenylacetate.

* * * * *

SEQUENCE LISTING

<160> NUMBER OF SEQ ID NOS: 13

<210> SEQ ID NO 1
<211> LENGTH: 373
<212> TYPE: PRT
<213> ORGANISM: Homo sapiens

<400> SEQUENCE: 1

Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Cys Val Glu Glu Leu Pro Glu Trp Asn Phe Asp Gly
    50                  55                  60

Ser Ser Thr Leu Gln Ser Glu Gly Ser Asn Ser Asp Met Tyr Leu Val
65                  70                  75                  80

```
Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Ser Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
            260                 265                 270

Ala Ile Glu Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
            340                 345                 350

Glu Ala Leu Ile Arg Thr Cys Leu Leu Asn Glu Thr Gly Asp Glu Pro
        355                 360                 365

Phe Gln Tyr Lys Asn
    370
```

<210> SEQ ID NO 2
<211> LENGTH: 372
<212> TYPE: PRT
<213> ORGANISM: Homo sapiens

<400> SEQUENCE: 2

```
Thr Thr Ser Ala Ser Ser His Leu Asn Lys Gly Ile Lys Gln Val Tyr
1               5                   10                  15

Met Ser Leu Pro Gln Gly Glu Lys Val Gln Ala Met Tyr Ile Trp Ile
            20                  25                  30

Asp Gly Thr Gly Glu Gly Leu Arg Cys Lys Thr Arg Thr Leu Asp Ser
        35                  40                  45

Glu Pro Lys Cys Val Glu Glu Leu Pro Glu Trp Asn Phe Asp Gly Ser
    50                  55                  60

Ser Thr Leu Gln Ser Glu Gly Ser Asn Ser Asp Met Tyr Leu Val Pro
```

```
65                  70                  75                  80

Ala Ala Met Phe Arg Asp Pro Phe Arg Lys Asp Pro Asn Lys Leu Val
                85                  90                  95

Leu Cys Glu Val Phe Lys Tyr Asn Arg Arg Pro Ala Glu Thr Asn Leu
            100                 105                 110

Arg His Thr Cys Lys Arg Ile Met Asp Met Val Ser Asn Gln His Pro
        115                 120                 125

Trp Phe Gly Met Glu Gln Glu Tyr Thr Leu Met Gly Thr Asp Gly His
    130                 135                 140

Pro Phe Gly Trp Pro Ser Asn Gly Phe Pro Gly Pro Gln Gly Pro Tyr
145                 150                 155                 160

Tyr Cys Gly Val Gly Ala Asp Arg Ala Tyr Gly Arg Asp Ile Val Glu
                165                 170                 175

Ala His Tyr Arg Ala Cys Leu Tyr Ala Gly Val Lys Ile Ala Gly Thr
            180                 185                 190

Asn Ala Glu Val Met Pro Ala Gln Trp Glu Phe Gln Ile Gly Pro Cys
        195                 200                 205

Glu Gly Ile Ser Met Gly Asp His Leu Trp Val Ala Arg Phe Ile Leu
    210                 215                 220

His Arg Val Cys Glu Asp Phe Gly Val Ile Ala Thr Phe Asp Pro Lys
225                 230                 235                 240

Pro Ile Pro Gly Asn Trp Asn Gly Ala Gly Cys His Thr Asn Phe Ser
                245                 250                 255

Thr Lys Ala Met Arg Glu Glu Asn Gly Leu Lys Tyr Ile Glu Glu Ala
            260                 265                 270

Ile Glu Lys Leu Ser Lys Arg His Gln Tyr His Ile Arg Ala Tyr Asp
        275                 280                 285

Pro Lys Gly Gly Leu Asp Asn Ala Arg Arg Leu Thr Gly Phe His Glu
    290                 295                 300

Thr Ser Asn Ile Asn Asp Phe Ser Ala Gly Val Ala Asn Arg Ser Ala
305                 310                 315                 320

Ser Ile Arg Ile Pro Arg Thr Val Gly Gln Glu Lys Lys Gly Tyr Phe
                325                 330                 335

Glu Asp Arg Arg Pro Ser Ala Asn Cys Asp Pro Phe Ser Val Thr Glu
            340                 345                 350

Ala Leu Ile Arg Thr Cys Leu Leu Asn Glu Thr Gly Asp Glu Pro Phe
        355                 360                 365

Gln Tyr Lys Asn
    370


<210> SEQ ID NO 3
<211> LENGTH: 1366
<212> TYPE: DNA
<213> ORGANISM: Artificial Sequence
<220> FEATURE:
<223> OTHER INFORMATION: cDNA sequence of SEQ ID NO 1

<400> SEQUENCE: 3

cgagagtggg agaagagcgg agcgtgtgag cagtactgcg gcctcctctc ctctcctaac      60

ctgctctcgc ggcctacctt tacccgcccg cctgctcggc gaccagaaca ccttccacca     120

tgaccacctc agcaagttcc cacttaaata aaggcatcaa gcaggtgtac atgtccctgc     180

ctcagggtga gaaagtccag gccatgtata tctggatcga tggtactgga gaaggactgc     240

gctgcaagac ccggaccctg gacagtgagc ccaagtgtgt ggaagagttg cctgagtgga     300
```

-continued

```
atttcgatgg ctccagtact ttacagtctg agggttccaa cagtgacatg tatctcgtgc    360

ctgctgccat gtttcgggac cccttccgta aggaccctaa caagctggtg ttatgtgaag    420

ttttcaagta caatcgaagg cctgcagaga ccaatttgag gcacacctgt aaacggataa    480

tggacatggt gagcaaccag cacccctggt ttggcatgga gcaggagtat accctcatgg    540

ggacagatgg gcaccccttt ggttggcctt ccaacggctt cccagggccc cagggtccat    600

attactgtgg tgtgggagca gacagagcct atggcaggga catcgtggag gcccattacc    660

gggcctgctt gtatgctgga gtcaagattg cggggactaa tgccgaggtc atgcctgccc    720

agtgggaatt tcagattgga ccttgtgaag gaatcagcat gggagatcat ctctgggtgg    780

cccgtttcat cttgcatcgt gtgtgtgaag actttggagt gatagcaacc tttgatccta    840

agcccattcc tgggaactgg aatggtgcag gctgccatac caacttcagc accaaggcca    900

tgcgggagga gaatggtctg aagtacatcg aggaggccat tgagaaacta agcaagcggc    960

accagtacca catccgtgcc tatgatccca agggaggcct ggacaatgcc cgacgtctaa   1020

ctggattcca tgaaacctcc aacatcaacg actttctgg tggtgtagcc aatcgtagcg   1080

ccagcatacg cattccccgg actgttggcc aggagaagaa gggttacttt gaagatcgtc   1140

gcccctctgc caactgcgac cccttttcgg tgacagaagc cctcatccgc acgtgtcttc   1200

tcaatgaaac cggcgatgag cccttccagt acaaaaatta agtggactag acctccagct   1260

gttgagcccc tcctagttct tcatcccact ccaactcttc cccctctccc agttgtcccg   1320

attgtaactc aaagggtgga atatcaaggt cgtttttttt cattcc                 1366
```

<210> SEQ ID NO 4
<211> LENGTH: 388
<212> TYPE: PRT
<213> ORGANISM: Artificial Sequence
<220> FEATURE:
<223> OTHER INFORMATION: GS protein grown in bacteria, used in Example 1

<400> SEQUENCE: 4

```
Met Gly Ser Ser His His His His His His Gly Gly Gly Gly Ser Met
1               5                   10                  15

Thr Thr Ser Ala Ser Ser His Leu Asn Lys Gly Ile Lys Gln Val Tyr
            20                  25                  30

Met Ser Leu Pro Gln Gly Glu Lys Val Gln Ala Met Tyr Ile Trp Ile
        35                  40                  45

Asp Gly Thr Gly Glu Gly Leu Arg Cys Lys Thr Arg Thr Leu Asp Ser
    50                  55                  60

Glu Pro Lys Cys Val Glu Glu Leu Pro Glu Trp Asn Phe Asp Gly Ser
65                  70                  75                  80

Ser Thr Leu Gln Ser Glu Gly Ser Asn Ser Asp Met Tyr Leu Val Pro
                85                  90                  95

Ala Ala Met Phe Arg Asp Pro Phe Arg Lys Asp Pro Asn Lys Leu Val
            100                 105                 110

Leu Cys Glu Val Phe Lys Tyr Asn Arg Arg Pro Ala Glu Thr Asn Leu
        115                 120                 125

Arg His Thr Cys Lys Arg Ile Met Asp Met Val Ser Asn Gln His Pro
    130                 135                 140

Trp Phe Gly Met Glu Gln Glu Tyr Thr Leu Met Gly Thr Asp Gly His
145                 150                 155                 160

Pro Phe Gly Trp Pro Ser Asn Gly Phe Pro Gly Pro Gln Gly Pro Tyr
                165                 170                 175
```

-continued

```
Tyr Cys Gly Val Gly Ala Asp Arg Ala Tyr Gly Arg Asp Ile Val Glu
            180                 185                 190

Ala His Tyr Arg Ala Cys Leu Tyr Ala Gly Val Lys Ile Ala Gly Thr
        195                 200                 205

Asn Ala Glu Val Met Pro Ala Gln Trp Glu Phe Gln Ile Gly Pro Cys
    210                 215                 220

Glu Gly Ile Ser Met Gly Asp His Leu Trp Val Ala Arg Phe Ile Leu
225                 230                 235                 240

His Arg Val Cys Glu Asp Phe Gly Val Ile Ala Thr Phe Asp Pro Lys
                245                 250                 255

Pro Ile Pro Gly Asn Trp Asn Gly Ala Gly Cys His Thr Asn Phe Ser
            260                 265                 270

Thr Lys Ala Met Arg Glu Glu Asn Gly Leu Lys Tyr Ile Glu Glu Ala
        275                 280                 285

Ile Glu Lys Leu Ser Lys Arg His Gln Tyr His Ile Arg Ala Tyr Asp
    290                 295                 300

Pro Lys Gly Gly Leu Asp Asn Ala Arg Arg Leu Thr Gly Phe His Glu
305                 310                 315                 320

Thr Ser Asn Ile Asn Asp Phe Ser Ala Gly Val Ala Asn Arg Ser Ala
                325                 330                 335

Ser Ile Arg Ile Pro Arg Thr Val Gly Gln Glu Lys Lys Gly Tyr Phe
            340                 345                 350

Glu Asp Arg Arg Pro Ser Ala Asn Cys Asp Pro Phe Ser Val Thr Glu
        355                 360                 365

Ala Leu Ile Arg Thr Cys Leu Leu Asn Glu Thr Gly Asp Glu Pro Phe
    370                 375                 380

Gln Tyr Lys Asn
385
```

<210> SEQ ID NO 5
<211> LENGTH: 1164
<212> TYPE: DNA
<213> ORGANISM: Artificial Sequence
<220> FEATURE:
<223> OTHER INFORMATION: bacterial optimised cDNA of the protein used in Example 1

<400> SEQUENCE: 5

```
atgggcagca gccaccacca tcaccaccac ggcggcggcg gtagcatgac cacctcggca     60

agcagccacc tgaataaagg catcaaacag gtgtatatgt ctctgccgca gggtgaaaaa    120

gttcaagcca tgtacatttg gatcgatggc accggtgaag gcctgcgttg caaaacccgc    180

acgctggact cagaaccgaa atgtgtggaa gaactgccgg aatggaactt tgatggtagc    240

tctacgctgc agtcggaagg cagtaattcc gacatgtatc tggttccggc ggccatgttt    300

cgtgatccgt tccgcaaaga cccgaacaaa ctggtgctgt gcgaagtttt taaatacaac    360

cgtcgcccgg cggaaaccaa tctgcgtcat acgtgtaaac gcattatgga tatggtcagc    420

aaccagcacc cgtggttcgg tatggaacaa gaatataccc tgatgggtac ggatggccat    480

ccgtttggtt ggccgagcaa tggtttcccg ggtccgcagg gtccgtatta ctgcggtgtc    540

ggcgcagatc gtgcttacgg tcgcgacatt gtggaagcac actatcgtgc ttgtctgtac    600

gcgggtgtta aaatcgccgg caccaatgca gaagtcatgc cggctcagtg ggaatttcaa    660

attggcccgt gcgaaggtat cagcatgggc gatcatctgt gggttgctcg tttcatcctg    720

caccgcgtct gtgaagattt tggtgtgatt gcgaccttcg acccgaaacc gatcccgggc    780
```

-continued

```
aactggaatg gtgctggctg ccataccaac tttagcacga aagcgatgcg tgaagaaaat    840

ggcctgaaat acatcgaaga agcaatcgaa aaactgtcta aacgtcatca gtatcacatt    900

cgcgcctacg atccgaaagg cggtctggac aacgcacgtc gcctgaccgg ttttcacgaa    960

acgagcaaca tcaatgattt ctctgcgggc gttgccaatc gctcagcctc gattcgtatc   1020

ccgcgcaccg tcggtcaaga gaaaaaaggc tattttgaag atcgtcgccc gagtgcaaac   1080

tgtgacccgt tctccgtgac ggaagccctg atccgcacct gtctgctgaa tgaaaccggc   1140

gatgaaccgt tccaatacaa aaat                                          1164
```

<210> SEQ ID NO 6
<211> LENGTH: 445
<212> TYPE: PRT
<213> ORGANISM: Lactobacillus acidophilus

<400> SEQUENCE: 6

```
Met Ser Lys Gln Tyr Thr Thr Glu Glu Ile Arg Lys Glu Val Ala Asp
1               5                   10                  15

Lys Asp Val Arg Phe Leu Arg Leu Cys Phe Thr Asp Ile Asn Gly Thr
            20                  25                  30

Glu Lys Ala Val Glu Val Pro Thr Ser Gln Leu Asp Lys Val Leu Thr
        35                  40                  45

Asn Asp Ile Arg Phe Asp Gly Ser Ser Ile Asp Gly Phe Val Arg Leu
    50                  55                  60

Glu Glu Ser Asp Met Val Leu Tyr Pro Asp Phe Ser Thr Trp Ser Val
65                  70                  75                  80

Leu Pro Trp Gly Asp Glu His Gly Gly Lys Ile Gly Arg Leu Ile Cys
                85                  90                  95

Ser Val His Met Thr Asp Gly Lys Pro Phe Ala Gly Asp Pro Arg Asn
            100                 105                 110

Asn Leu Lys Arg Val Leu Gly Glu Met Lys Glu Ala Gly Phe Asp Thr
        115                 120                 125

Phe Asp Ile Gly Phe Glu Met Glu Phe His Leu Phe Lys Leu Asp Glu
    130                 135                 140

Asn Gly Asn Trp Thr Thr Glu Val Pro Asp His Ala Ser Tyr Phe Asp
145                 150                 155                 160

Met Thr Ser Asp Asp Glu Gly Ala Arg Cys Arg Arg Glu Ile Val Glu
                165                 170                 175

Thr Leu Glu Glu Ile Gly Phe Glu Val Glu Ala Ala His His Glu Val
            180                 185                 190

Gly Asp Gly Gln Gln Glu Ile Asp Phe Arg Phe Asp Asp Ala Leu Thr
        195                 200                 205

Thr Ala Asp Arg Cys Gln Thr Phe Lys Met Val Ala Arg His Ile Ala
    210                 215                 220

Arg Lys His Gly Leu Phe Ala Thr Phe Met Ala Lys Pro Val Glu Gly
225                 230                 235                 240

Gln Ala Gly Asn Gly Met His Asn Asn Met Ser Leu Phe Lys Asn Lys
                245                 250                 255

His Asn Val Phe Tyr Asp Lys Asp Gly Glu Phe His Leu Ser Asn Thr
            260                 265                 270

Ala Leu Tyr Phe Leu Asn Gly Ile Leu Glu His Ala Arg Ala Ile Thr
        275                 280                 285

Ala Ile Gly Asn Pro Thr Val Asn Ser Tyr Lys Arg Leu Ile Pro Gly
    290                 295                 300
```

-continued

```
Phe Glu Ala Pro Val Tyr Ile Ala Trp Ala Ala Lys Asn Arg Ser Pro
305                 310                 315                 320

Leu Val Arg Ile Pro Ser Ala Gly Glu Ile Asn Thr Arg Leu Glu Met
                325                 330                 335

Arg Ser Ala Asp Pro Thr Ala Asn Pro Tyr Leu Leu Leu Ala Ala Cys
            340                 345                 350

Leu Thr Ala Gly Leu Lys Gly Ile Lys Glu Gln Lys Met Pro Met Lys
        355                 360                 365

Pro Val Glu Glu Asn Ile Phe Glu Met Thr Glu Glu Glu Arg Ala Glu
    370                 375                 380

His Gly Ile Lys Pro Leu Pro Thr Thr Leu His Asn Ala Ile Lys Ala
385                 390                 395                 400

Phe Lys Glu Asp Asp Leu Ile Lys Ser Ala Leu Gly Glu His Leu Thr
                405                 410                 415

His Ser Phe Ile Glu Ser Lys Glu Leu Glu Trp Ser Lys Tyr Ser Gln
            420                 425                 430

Ser Val Ser Asp Trp Glu Arg Gln Arg Tyr Met Asn Trp
        435                 440                 445


<210> SEQ ID NO 7
<211> LENGTH: 356
<212> TYPE: PRT
<213> ORGANISM: Zea mays

<400> SEQUENCE: 7

Met Ala Cys Leu Thr Asp Leu Val Asn Leu Asn Leu Ser Asp Asn Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Ser Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Cys Tyr Thr
                85                  90                  95

Pro Ala Gly Glu Pro Ile Pro Thr Asn Lys Arg Tyr Asn Ala Ala Lys
            100                 105                 110

Ile Phe Ser Ser Pro Glu Val Ala Ala Glu Glu Pro Trp Tyr Gly Ile
        115                 120                 125

Glu Gln Glu Tyr Thr Leu Leu Gln Lys Asp Thr Asn Trp Pro Leu Gly
    130                 135                 140

Trp Pro Ile Gly Gly Phe Pro Gly Pro Gln Gly Pro Tyr Tyr Cys Gly
145                 150                 155                 160

Ile Gly Ala Glu Lys Ser Phe Gly Arg Asp Ile Val Asp Ala His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ser Gly Asp Gln Val Trp Val Ala Arg Tyr Ile Leu Glu Arg Ile
    210                 215                 220

Thr Glu Ile Ala Gly Val Val Val Thr Phe Asp Pro Lys Pro Ile Pro
225                 230                 235                 240
```

```
Gly Asp Trp Asn Gly Ala Gly Ala His Thr Asn Tyr Ser Thr Glu Ser
                245                 250                 255

Met Arg Lys Glu Gly Gly Tyr Glu Val Ile Lys Ala Ala Ile Glu Lys
            260                 265                 270

Leu Lys Leu Arg His Arg Glu His Ile Ala Ala Tyr Gly Glu Gly Asn
        275                 280                 285

Glu Arg Arg Leu Thr Gly Arg His Glu Thr Ala Asp Ile Asn Thr Phe
    290                 295                 300

Ser Trp Gly Val Ala Asn Arg Gly Ala Ser Val Arg Val Gly Arg Glu
305                 310                 315                 320

Thr Glu Gln Asn Gly Lys Gly Tyr Phe Glu Asp Arg Arg Pro Ala Ser
                325                 330                 335

Asn Met Asp Pro Tyr Val Val Thr Ser Met Ile Ala Glu Thr Thr Ile
            340                 345                 350

Ile Trp Lys Pro
        355


<210> SEQ ID NO 8
<211> LENGTH: 4
<212> TYPE: PRT
<213> ORGANISM: Artificial Sequence
<220> FEATURE:
<223> OTHER INFORMATION: linker

<400> SEQUENCE: 8

Gly Gly Gly Ser
1


<210> SEQ ID NO 9
<211> LENGTH: 5
<212> TYPE: PRT
<213> ORGANISM: Artificial Sequence
<220> FEATURE:
<223> OTHER INFORMATION: linker

<400> SEQUENCE: 9

Gly Gly Gly Gly Ser
1               5


<210> SEQ ID NO 10
<211> LENGTH: 6
<212> TYPE: PRT
<213> ORGANISM: Artificial Sequence
<220> FEATURE:
<223> OTHER INFORMATION: poly(his) tag

<400> SEQUENCE: 10

His His His His His His
1               5


<210> SEQ ID NO 11
<211> LENGTH: 17
<212> TYPE: PRT
<213> ORGANISM: Artificial Sequence
<220> FEATURE:
<223> OTHER INFORMATION: GS sequence

<400> SEQUENCE: 11

Gly Gly Gly Ser His His His His His His Gly Gly Gly Gly Ser Gly
1               5                   10                  15

Ser
```

-continued

```
<210> SEQ ID NO 12
<211> LENGTH: 15
<212> TYPE: PRT
<213> ORGANISM: Artificial Sequence
<220> FEATURE:
<223> OTHER INFORMATION: N terminal of human recombinant GS

<400> SEQUENCE: 12

Gly Gly Gly Ser His His His His His His Gly Gly Gly Gly Ser
1               5                   10                  15


<210> SEQ ID NO 13
<211> LENGTH: 4
<212> TYPE: PRT
<213> ORGANISM: Artificial Sequence
<220> FEATURE:
<223> OTHER INFORMATION: linker

<400> SEQUENCE: 13

Gly Gly Ser Gly
1
```